United States Patent
Yates et al.

(10) Patent No.: US 11,576,970 B2
(45) Date of Patent: Feb. 14, 2023

(54) PHARMACEUTICAL FORMULATIONS

(71) Applicant: UCB BIOPHARMA SPRL, Brussels (BE)

(72) Inventors: Andrew Jeffrey Yates, Victoria (AU); James Gregory Clipstone, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 0 days.

(21) Appl. No.: 16/083,321

(22) PCT Filed: Mar. 9, 2017

(86) PCT No.: PCT/EP2017/055594
§ 371 (c)(1),
(2) Date: Sep. 7, 2018

(87) PCT Pub. No.: WO2017/153541
PCT Pub. Date: Sep. 14, 2017

(65) Prior Publication Data
US 2019/0083617 A1 Mar. 21, 2019

(30) Foreign Application Priority Data
Mar. 10, 2016 (GB) ..................... 1604124

(51) Int. Cl.
| | | |
|---|---|---|
| *A61K 39/395* | (2006.01) |
| *C07K 16/22* | (2006.01) |
| *A61K 9/00* | (2006.01) |
| *A61K 47/18* | (2017.01) |
| *A61K 9/08* | (2006.01) |
| *A61K 47/20* | (2006.01) |
| *A61K 47/40* | (2006.01) |
| *A61K 39/00* | (2006.01) |

(52) U.S. Cl.
CPC ...... *A61K 39/39591* (2013.01); *A61K 9/0019* (2013.01); *A61K 9/08* (2013.01); *A61K 47/183* (2013.01); *A61K 47/20* (2013.01); *A61K 47/40* (2013.01); *C07K 16/22* (2013.01); *A61K 2039/54* (2013.01); *C07K 2317/24* (2013.01)

(58) Field of Classification Search
None
See application file for complete search history.

(56) References Cited

U.S. PATENT DOCUMENTS

| | | |
|---|---|---|
| 4,331,647 A | 5/1982 | Goldenberg |
| 4,376,110 A | 3/1983 | David et al. |
| 4,411,993 A | 10/1983 | Gillis |
| 4,427,115 A | 1/1984 | Laipply |
| 4,543,439 A | 9/1985 | Frackelton, Jr. et al. |
| RE32,011 E | 10/1985 | Zimmerman et al. |
| 4,837,440 A | 6/1989 | Burtscher et al. |
| 4,902,614 A | 2/1990 | Wakabayashi et al. |
| 5,070,108 A | 12/1991 | Margolis |
| 5,145,684 A | 9/1992 | Liversidge et al. |
| 5,223,409 A | 6/1993 | Ladner et al. |
| 5,399,363 A | 3/1995 | Liversidge et al. |
| 5,453,492 A | 9/1995 | Butzow et al. |
| 5,466,468 A | 11/1995 | Schneider et al. |
| 5,543,158 A | 8/1996 | Gref et al. |
| 5,552,157 A | 9/1996 | Yagi et al. |
| 5,565,213 A | 10/1996 | Nakamori et al. |
| 5,567,434 A | 10/1996 | Szoka, Jr. |
| 5,571,714 A | 11/1996 | Dasch et al. |
| 5,627,052 A | 5/1997 | Schrader et al. |
| 5,641,515 A | 6/1997 | Ramtoola |
| 5,698,426 A | 12/1997 | Huse |
| 5,738,868 A | 4/1998 | Shinkarenko et al. |
| 5,780,263 A | 7/1998 | Hastings et al. |
| 5,795,587 A | 8/1998 | Gao et al. |
| 5,795,965 A | 8/1998 | Tsuchiya et al. |
| 5,811,238 A | 9/1998 | Stemmer et al. |
| 5,830,721 A | 11/1998 | Stemmer et al. |
| 5,837,458 A | 11/1998 | Minshull et al. |
| 5,877,397 A | 3/1999 | Lonberg et al. |

(Continued)

FOREIGN PATENT DOCUMENTS

| | | | | |
|---|---|---|---|---|
| EP | 2399604 A1 | * | 12/2011 | ............. A61P 29/00 |
| JP | 4-141095 | | 5/1992 | |
| WO | WO-1991/013152 | | 9/1991 | |
| WO | WO-1992/001047 | | 1/1992 | |
| WO | WO-1992/002551 | | 2/1992 | |

(Continued)

OTHER PUBLICATIONS

A diagram of a relevant part of the human genome (D64), citation in Appeal, European Patent No. 1133558, dated Apr. 15, 2010.

(Continued)

*Primary Examiner* — Yunsoo Kim
(74) *Attorney, Agent, or Firm* — Marshall, Gerstein & Borun LLP

(57) ABSTRACT

The invention relates to a liquid pharmaceutical formulation comprising an antibody or antigen-binding fragment thereof, cyclodextrin and methionine. In addition, it relates to a method for reducing precipitation of an antibody or an antigen-binding fragment thereof in a liquid pharmaceutical formulation through addition of methionine and cyclodextrin. In particular, the liquid pharmaceutical formulations comprises an anti-sclerostin antibody, hydroxypropyl-gamma cyclodextrin and methionine and may be used in the treatment of a bone disorder associated with at least one of low bone formation, low bone mineral density, low bone mineral content, low bone mass, low bone quality and low bone strength, and especially for treating osteoporosis. Furthermore, the invention relates to a method of reducing inflammation at injection site in a mammalian subject comprising administering a therapeutically effective amount of a liquid pharmaceutical formulation comprising an antibody or antigen-binding fragment thereof, cyclodextrin and methionine.

12 Claims, 3 Drawing Sheets

Specification includes a Sequence Listing.

(56) References Cited

U.S. PATENT DOCUMENTS

| | | | |
|---|---|---|---|
| 6,054,561 A | 4/2000 | Ring | |
| 6,057,421 A | 5/2000 | Muller et al. | |
| 6,117,911 A | 9/2000 | Grainger et al. | |
| 6,133,426 A | 10/2000 | Gonzalez et al. | |
| 6,180,370 B1 | 1/2001 | Queen et al. | |
| 6,207,153 B1 | 3/2001 | Dan et al. | |
| 6,395,511 B1 | 5/2002 | Brunkow et al. | |
| 6,489,445 B1 | 12/2002 | Brunkow et al. | |
| 6,495,736 B1 | 12/2002 | Brunkow et al. | |
| 6,703,199 B1 | 3/2004 | Koide | |
| 6,803,453 B1 | 10/2004 | Brunkow et al. | |
| 6,806,055 B2 | 10/2004 | Berman et al. | |
| 6,815,201 B2 | 11/2004 | Pinter | |
| 6,818,748 B2 | 11/2004 | Fulton et al. | |
| 7,192,583 B2 | 3/2007 | Brunkow et al. | |
| 7,226,902 B2 | 6/2007 | Winkler et al. | |
| 7,381,409 B2 | 6/2008 | Winkler et al. | |
| 7,572,899 B2 | 8/2009 | Brunkow et al. | |
| 7,578,999 B2 | 8/2009 | Winkler et al. | |
| 7,592,429 B2 * | 9/2009 | Paszty | A61P 19/10 530/388.24 |
| 7,642,238 B2 | 1/2010 | Shaughnessy | |
| 7,758,858 B2 | 7/2010 | Brunkow et al. | |
| 7,846,427 B2 * | 12/2010 | Del Curto | A61K 38/215 424/85.6 |
| 7,868,134 B2 | 1/2011 | Winkler et al. | |
| 7,872,106 B2 | 1/2011 | Paszty et al. | |
| 8,178,099 B2 | 5/2012 | Ellies | |
| 8,383,801 B2 | 2/2013 | Paszty et al. | |
| 8,563,271 B2 | 10/2013 | Winkler et al. | |
| 8,637,643 B2 | 1/2014 | Latham | |
| 8,715,663 B2 | 5/2014 | Paszty et al. | |
| 8,992,911 B2 | 3/2015 | Winkler et al. | |
| 9,011,856 B2 | 4/2015 | Winkler et al. | |
| 9,296,812 B2 | 3/2016 | Paszty et al. | |
| 9,353,174 B2 | 5/2016 | Paszty et al. | |
| 2003/0165410 A1 | 9/2003 | Taylor | |
| 2003/0166247 A1 | 9/2003 | Brunkow et al. | |
| 2003/0186915 A1 | 10/2003 | Pan et al. | |
| 2003/0229041 A1 | 12/2003 | Sutherland et al. | |
| 2004/0009535 A1 | 1/2004 | Brunkow et al. | |
| 2004/0023356 A1 | 2/2004 | Krumlauf et al. | |
| 2004/0058321 A1 | 3/2004 | Brunkow et al. | |
| 2004/0141875 A1 | 7/2004 | Doshi | |
| 2004/0146888 A1 | 7/2004 | Paszty et al. | |
| 2004/0158045 A1 | 8/2004 | Brunkow et al. | |
| 2005/0014650 A1 | 1/2005 | Seitz et al. | |
| 2005/0085418 A1 | 4/2005 | Winkler et al. | |
| 2005/0106683 A1 | 5/2005 | Winkler et al. | |
| 2005/0238646 A1 | 10/2005 | Ledbetter et al. | |
| 2006/0233801 A1 | 10/2006 | Brunkow et al. | |
| 2007/0072797 A1 | 3/2007 | Robinson et al. | |
| 2007/0110747 A1 | 5/2007 | Paszty et al. | |
| 2007/0292444 A1 | 12/2007 | Krumlauf et al. | |
| 2008/0182788 A1 | 7/2008 | Brunkow et al. | |
| 2008/0234219 A1 | 9/2008 | Brunkow et al. | |
| 2009/0074763 A1 | 3/2009 | Padhi et al. | |
| 2009/0117118 A1 | 5/2009 | Winkler et al. | |
| 2009/0304713 A1 | 12/2009 | Paszty et al. | |
| 2010/0015665 A1 | 1/2010 | Latham et al. | |
| 2010/0036091 A1 | 2/2010 | Robinson et al. | |
| 2010/0151524 A1 | 6/2010 | Winkler et al. | |
| 2011/0044978 A1 | 2/2011 | Ke et al. | |
| 2011/0097342 A1 | 4/2011 | Paszty et al. | |
| 2011/0150866 A1 | 6/2011 | Brunkow et al. | |
| 2012/0238942 A1 | 9/2012 | Horstmann et al. | |
| 2013/0202620 A1 * | 8/2013 | Osslund | A61P 19/10 424/172.1 |

FOREIGN PATENT DOCUMENTS

| | | | |
|---|---|---|---|
| WO | WO-1992/006693 | 4/1992 | |
| WO | WO-1995/030003 | 11/1995 | |
| WO | WO-1996/004375 | 2/1996 | |
| WO | WO-1998/021335 | 5/1998 | |
| WO | WO-1999/003996 | 1/1999 | |
| WO | WO-1999/006554 | 2/1999 | |
| WO | WO-1999/015556 | 4/1999 | |
| WO | WO-2000/032773 | 6/2000 | |
| WO | WO-2000/044777 | 8/2000 | |
| WO | WO-2000/075317 | 12/2000 | |
| WO | WO-2001/064885 | 9/2001 | |
| WO | WO-2001/092308 | 12/2001 | |
| WO | WO-2001/098491 | 12/2001 | |
| WO | WO-2002/024888 | 3/2002 | |
| WO | WO-2002/030463 | 4/2002 | |
| WO | WO-2003/050513 | 6/2003 | |
| WO | WO-2003/087763 | 10/2003 | |
| WO | WO-2003/106657 | 12/2003 | |
| WO | WO-2004/082608 | 9/2004 | |
| WO | WO-2004/094477 | 11/2004 | |
| WO | WO-2004/098491 | 11/2004 | |
| WO | WO-2005/003158 | 1/2005 | |
| WO | WO-2005/014650 | 2/2005 | |
| WO | WO-2005/058346 | 6/2005 | |
| WO | WO-2005/110466 | 11/2005 | |
| WO | WO-2005/115356 | 12/2005 | |
| WO | WO-2006/015373 | 2/2006 | |
| WO | WO-2006/065746 | 6/2006 | |
| WO | WO-2006/083689 | 8/2006 | |
| WO | WO-2006/102070 | 9/2006 | |
| WO | WO-2006/119062 | 11/2006 | |
| WO | WO-2006/119107 | 11/2006 | |
| WO | WO-2007/080129 | 7/2007 | |
| WO | WO-2007/109221 | 9/2007 | |
| WO | WO-2008/061013 | 5/2008 | |
| WO | WO-2008/092894 | 8/2008 | |
| WO | WO-2008/115732 | 9/2008 | |
| WO | WO-2008/133722 | 11/2008 | |
| WO | WO-2009/026558 | 2/2009 | |
| WO | WO-2009/039175 | 3/2009 | |
| WO | WO-2009/047356 | 4/2009 | |
| WO | WO-2009/056634 | 5/2009 | |
| WO | WO-2009/079471 | 6/2009 | |
| WO | WO-2009/131553 | 10/2009 | |
| WO | WO-2009/149189 | 12/2009 | |
| WO | WO-2010/057107 | 5/2010 | |
| WO | WO-2010057107 A1 * | 5/2010 | A61P 29/00 |
| WO | WO-2010/100179 | 9/2010 | |
| WO | WO-2010/100200 | 9/2010 | |
| WO | WO-2010/115932 | 10/2010 | |
| WO | WO-2010/130830 | 11/2010 | |
| WO | WO-2011/143307 | 11/2011 | |
| WO | WO-2012/028683 | 3/2012 | |
| WO | WO-2012/058393 | 5/2012 | |

OTHER PUBLICATIONS

Abbas et. al. (Eds.), Cellular and Molecular Immunology, Third Edition. Section II, p. 54 (1997).

Alberts et. al. (Eds.), Molecular Biology of the Cell, Third Edition, Chapter 23, p. 1212 (1994).

Albertsen et. al., A physical map and candidate genes in the BRCA1 region on chromosome 17q12-21. *Nat. Genet.*, 7:472-9 (1994).

Alting-Mees et. al., Monoclonal antibody expression libraries: A rapid alternative to hybridomas. *Strat. Molec. Biol.*, 3:1-9 (1990).

Alves et. al., Sclerosteosis: A marker of Dutch ancestry? *Rev. Bras. Genet.*, 4:825-34 (1982).

Andersson et. al., Molecular genetics and pathophysiology of 17β-hydroxysteriod dehydrogenase 3 deficiency. *J. Clin. Endrocrinol. Metab.*, 81(1): 130-6 (1996).

Angal et. al., A single amino acid substitution abolishes the heterogeneity of chimeric mouse/human (IgG4) antibody. *Mol. Immunol.*, 30(1):105-8 (1993).

Annex EW6 to Declaration filed in connection with the European Patent EP 1133558 Opposition, Expert opinion of Prof. Dr. Edgar Wingender, dated Sep. 24, 2009.

(56) References Cited

OTHER PUBLICATIONS

Annex regarding the purported relevance of gene/peptides mentioned by Professor Arnett, dated Mar. 18, 2011.
Anonymous, Amgen presents denosumab and sclerostin antibody data at American Society for Bone and Mineral Research Annual Meeting. Amgen Media Press Release. <www.amgen.com/media/media_pr_detail.jsp?releaseID=907028> (2006).
Anonymous, UCB on track. UCB News <http://hugin.info/133973/R/1176122/233395.pdf> (2007).
Arnett et al., Effect of pH on bone resorption by rat osteoclasts in vitro, *Endocrinol.*, 119(1):119-24 (1986).
Ardery, Liquid Chromatography—Mass Spectrometry: An Introduction (2003).
Arpino et al., Combined liquid chromatography mass spectrometry Part I. Coupling by means of moving belt interface, Mass Spectrometry Rev. 8:35-55 (1989).
Attana Application Example, cited in Opposition against European Patent No. 1721979 by Opponent: Novartis AG, dated Jun. 15, 2011.
Avsian-Kretchmer et. al., Comparative genomic analysis of the eight-membered ring cystine knot-containing bone morphogenetic protein antagonists. *Molec. Endocrinol.*, 18(1):1-12 (2004).
Babcook et. al., A novel strategy for generating monoclonal antibodies from single, isolated lymphocytes producing antibodies of defined specificities. *Proc. Natl. Acad. Sci. USA*, 93:7843-8 (1996).
Baines et. al., Purification of immunoglobulin G (IgG). *Meth. Molec. Biol.*, 10:79-104 (1992).
Balemans et. al., Extracellular regulation of BMP signaling in vertebrates: A cocktail of modulators. *Dev. Biol.*, 250:231-50 (2002).
Balemans et. al., Increased bone density in sclerosteosis is due to the deficiency of a novel secreted protein (SOST). *Hum. Mol. Genet.*, 10:537-43 (2001).
Balemans et. al., Localization of the gene for sclerosteosis to the van Buchem disease-gene region on chromosome 17q12-q21. *Am. J. Hum. Genet.*, 64:1661-9 (1999).
Balint et. al., Antibody engineering by parsimonious mutagenesis. *Gene*, 137(1):109-18 (1993).
Bateman et. al., Granulins: The structure and function of an emerging family of growth factors. *J. Endocrinol.*, 158: 145-51 (1998).
Baxevanis (Ed.) et. al., Bioinformatics: A practical guide to the analysis of genes and proteins, John Wiley & Sons, Inc. p. 234 (1998).
Bee et al., Exploring the Dynamic Range of the Kinetic Exclusion Assay in Characterizing Antigen-Antibody Interactions, PLoS ONE, (2012).
Beighton et. al., Heterozygous manifestations in the heritable disorders of the skeleton. *Pediatr. Radiol.*, 27: 397-401 (1997).
Beighton et. al., The clinical features of sclerosteosis. *Clin. Genet.*, 25:175-81 (1984).
Beighton et. al., The syndromic status of sclerosteosis and van Buchem disease. *Ann. Intern. Med.*, 84:393-7 (1976).
Bellows et. al., Parathyroid hormone reversibly suppresses the differentiation of osteoprogenitor cells in functional osteoblasts. *Endocrinol.*, 127(6): 3111-6 (1990).
Bendayan, Possibilities of false immunocytochemical results generated by the use of monoclonal antibodies: The example of the anti-proinsulin antibody. *J. Histochem. Cytochem.*, 43(9):881-6 (1995).
Bendig, Humanization of rodent monoclonal antibodies by CDR grafting. *Methods*, 8:83-93 (1995).
Bergfeld et. al., Release of ATP from human erythrocytes in response to a brief period of hypoxia and hypercapnia. *Cardiovascular Res.*, 26: 40-7 (1992).
Berman et. al., The protein data bank. *Acta. Cryst.*, 58(1):899-907 (2002).
Bigger versions of Figures from Declaration of Professor Teresa Attwood, citation in Appeal, European Patent No. 1133558, dated Apr. 13, 2010.
Bird et. al., Single-chain antigen-binding proteins. *Science*, 242:423-6 (1988).
Birren et. al., EMBL sequence database accession No. AC003098.2, Nov. 14, 1997.
Bishop (Ed.), Guide to Human Genome Computing, Second Edition, Academic Press, Chapter 1: Introduction to human genome computer via the world wide web, pp. 1-14 (2003).
Black et. al., A somatic cell hybrid map of the long arm of human chromosome 17, containing the familial breast cancer ILocus (BRCAI). *Am. J. Hum. Genet.*, 52:702-10 (1993).
Blum et. al., Study plan for German students in the summer of 1998, University Bioinformatik lecture announcement (1998).
Boden et. al., Glucocorticoid-induced differentiation of fetal rat calvarial osteoblasts is mediated by bone morphogenetic protein-6. *Endocrinology*, 138(7):2820-8 (1997).
Boerner et. al., Production of antigen-specific human monoclonal antibodies from in vitro-primed human splenocytes. *J. Immunol.*, 147:86-95 (1991).
Bonaldo et. al., EMBL Sequence Database Accession No. AI113131, Sep. 4, 1998.
Bonaldo et. al., Normalization and subtraction: Two approaches to facilitate gene discovery. *Genome Res.*, 6(9):791-806 (1996).
Bondestam, Ligands & Signaling Components of the Transforming Growth Factor, Helsinki University Biomedical Dissertations (2002).
Bork et. al., Go hunting in sequence databases by watch out for the traps. *Trends Genet.*, 12: 425-7 (1996).
Borrok et al., Revisiting the Role of Glycosylation in the Structure of Human IgG Fc, *ACS Chemical Biology*, 1596-602 (2012).
Bos et. al., Ras ongogenes in human cancer: A review. *Cancer Res.*, 49: 4682-9 (1989).
Bost et. al., Antibodies against a peptide sequence within the HIV envelope protein crossreacts with human interleukin-2. *Immunol. Invest.*, 17(6&7):577-86 (1988).
Bostrom et. al., Ligand and signaling components of the transforming growth factor β family. *J. Orth. Res.*, 13:357-67 (1995).
Bottcher et. al., NCBI Sequence database accession No. NM_004329, Aug. 2, 2009.
Bouffard et. al., A physical map of human chromosome 7: An integrated YAC contig map with average STS spacing of 79 kb. *Genome Res.*, 7: 673-92 (1997).
Bowie et. al., A method to identify protein sequences that fold into a known three-dimensional structure. *Science*, 253:164-70 (1991).
Bowie et. al., Deciphering the message in protein sequences: Tolerance to amino acid substitutions. *Science*, 247(4948):1306-10 (1990).
Bradley et. al., Modifying the mouse: Design and desire. *Bio/Technology*, 10:534-9 (1992).
Brandao-Burch et. al., Acidosis inhibits bone formation by osteoblasts in vitro by preventing mineralization. *Calcif. Tissue Int.*, 77: 167-74 (2005).
Brenner et. al., Population statistics of protein structures: Lessons from structural classifications. *Curr. Op. Struct. Biol.*, 7(3):369-76 (1997).
Brown, Hybridization analysis of DNA blots, *Current Protocols in Protein Science*, 13:A.4H.1-A.4H.9 (1990).
Brown, Hybridization analysis of DNA blots, *Current Protocols in Protein Science*, 2.10.1-2.10.16 (2000).
Bruggemann et. al., Production of human antibody repertoires in transgenic mice. *Curr. Opin. Biotechnol.*, 8:455-8 (1997).
Brunkow et. al., Bone dysplasia sclerosteosis results from loss of the SOST gene product, a novel cysteine knot-containing protein. *Am. J. Hum. Genet.*, 68:577-89 (2001).
Burton et. al., Human antibodies from combinatorial libraries. *Adv. Immunol.*, 57:191-280 (1994).
Butcher et. al., Increased salt concentration reversibly destabilizes p53 quaternary structure and sequence-specific DNA binding. *Biochem. J.*, 298: 513-6 (1994).
Byrne et. al., CD4+CD45RBHi T cell transfer induced colitis in mice is accompanied by osteopenia which is treatable with recombinant human osteoprotegerin. *Gut.*, 54:78-86 (2005).
Campbell et. al., Totipotency or multipotentiality of cultured cells: Applications and progress. *Theriogenology*, 47:63-72 (1997).
Caverzasio et. al., Characteristics and regulation of Pi transport in osteogenic cells for bone metabolism. *Kindey Int.*, 49: 975-80 (1996).

(56) References Cited

OTHER PUBLICATIONS

Chan et. al., A new paradigm in the treatment of osteoporosis: Wnt pathway proteins and their antagonists. *Curr. Opin. Invest. Drugs*, 8:293-8 (2007).
Chandran et. al., Recent trends in drug delivery systems: Liposomal drug delivery system—Preparation and characterization. *Indian J. Exp. Biol.*, 35(8):801-9 (1997).
Charlier et. al., A pore mutation in a novel KQT-like potassium channel gene in an idiopathic epilepsy family. *Nat. Genet.*, 18:53-5 (1998).
Chenu et. al., Glutamate receptors are expressed by bone cells and are involved in bone resorption. *Bone*, 22(4): 295-9 (1998).
Chou et. al., Empirical predication of protein conformation. *Ann. Rev. Biochem.*, 47:251-76 (1979).
Chou et. al., Prediction of the secondary structure of proteins from their amino acid sequence. *Adv. Enzymol. Relat. Areas Mol. Biol.*, 47:145-8 (1978).
Citation in Opposition Procedure against European Patent No. 2556841. Declaration Under 37 CFR 1.132 (Chris Paszty, Ph.D.) dated Jun. 14, 2012, submitted Jul. 25, 2017.
Clark, Antibody humanization: A case of the 'Emperor's New Clothes'?. *Immunology Today*, 21(8):397-402 (2000).
Cogan et. al., NCBI Sequence Database Accession No. NM_033346, Jul. 19, 2005.
Collins, Identifying human disease genes by positional cloning. The Harvey Lectures, Series 86:149-64 (1992).
Collins, Positional cloning moves from perditional to traditional. *Nat. Genet.*, 9:347-50 (1995).
Colman, Effects of amino acid sequence changes on antibody-antigen interactions. *Biomolec. Res. Inst.*, 55:33-6(1994).
Communication from the European Patent Office providing an "Observation by a Third Party according to Article 115 EPC" submitted in connection with the Opposition to European Patent No. 1 133 558, dated Dec. 3, 2008.
Cook et. al., Structural basis for a functional antagonist in the transforming growth factor 3 superfamily. *J. Biol. Chem.*, 280(48):40177-86 (2005).
Minutes of the first instance of OP oral proceeding dated Mar. 5, 2018.
Cormier, Markers of bone metabolism. *Curr. Opin. in Rheu.*, 7:243-8 (1995).
Couvreur et. al., Polyalkylcyanoacrylates as colloidal drug carriers. *Crit. Rev. Ther. Drug Carrier Syst.*, 5(1):1-20 (1988).
Craig et. al., Sclerostin binds and regulates the activity of cysteine rich protein 61. *Biochem. Biophys. Res. Commun.*, 293(1): 36-40 (2010).
Craig et. al., Sclerostin-erbB-3 interactions: Modulation of erbB-3 activity by sclerostin. *Biochem. Biophys. Res. Commun.*, 402: 421-4 (2010).
Crameri et. al., DNA shuffling of a family of genes from diverse species accelerates directed evolution. *Nature*, 391:288-91 (1998).
Dall'Acqua et. al., Antibody humanization by framework shuffling. *Methods*, 36(1):43-60 (2005).
Davies, et. al., Affinity improvement of single antibody VH domains: Residues in all three hypervariable regions affect antigen binding. *Immunotechnology*, 2(3): 169-79 (1996).
Davis et al., Cyclodextrin-based pharmaceutics: past, present and future. *Nature Reviews—Drug Discovery*, 3(12):1023-35 (2004).
de Jong et. al., Evolution of the α-crystallin/small heat-shock protein family. *Mol. Biol. Evol.*, 10(1): 103-26 (1993).
Dean et. al., Matrix vesicles produced by osteoblast-like cells in culture become significantly enriched in proteoglycan-degrading metalloproteinases after addition of β-glycerophosphate and ascorbic acid. *Calcif. Tissue*, 54: 399-408 (1994).
Declaration filed in connection with the European Patent EP 1133558 Opposition, Expert opinion of Dr. Auristela Freire de Paes Alves, Ph.D., dated Sep. 9, 2009.
Declaration filed in connection with the European Patent EP 1133558 Opposition, Expert opinion of Dr. Walter Sebald, dated Sep. 24, 2009.
Declaration filed in connection with the European Patent EP 1133558 Opposition, Expert opinion of Prof. Dr. Edgar Wingender, dated Sep. 24, 2009.
Declaration filed in connection with the European Patent EP 1133558 Opposition, Expert opinion of Prof. Dr. Thomas Muller, dated Sep. 23, 2009.
Declaration of Alistair J. Henry, citation in Appeal, European Patent No. 1133558, dated Apr. 2, 2010.
Declaration of Dr. Martyn Robinson, submitted in Opposition to European Patent No. 1133558, dated Jan. 13, 2008.
Declaration of Dr. Mary E. Brunkow, submitted in Opposition to European Patent No. 1133558, dated Jan. 9, 2008.
Declaration of Dr. Paszty dated Nov. 12, 2017.
Declaration of Dr. Raymond Dalgleish dated Dec. 8, 2011, citation in Appeal, European Patent No. 1133558.
Declaration of Dr. Robinson dated Jan. 5, 2015.
Declaration of Prof. Edgar Wingender filed in connection with that Opposition regarding European Patent EP 1133558 B1, dated Mar. 10, 2011.
Declaration of Professor Teresa Attwood, citation in Appeal, European Patent No. 1133558, dated Apr. 13, 2010.
Declaration of Tim Arnett, citation in Appeal. European Patent No. 1133558, dated Apr. 2, 2010.
Delmas et. al., The use of biochemical markers of bone turnover in osteoporosis. *Osteoporosis International*, Suppl. 6:S2-17 (2000).
Diagram of the candidate interval, citation by Propriator in Opposition against European Patent No. 1721979 on Feb. 20, 2012.
Drake et al., Current Trends in Monoclonal Antibody Development and Manufacturing, Chapter 11, "Characterizing High Affinity Antigen/Antibody Complexes by Kinetic and Equilibrium Based Methods", pp. 179-192(2010).
Ducy et. al., 5-HT and bone biology. *Curr. Opin. Pharmacol.*, 11: 34-8 (2011).
Ducy et. al., Genetic control of cell differentiation in the skeleton. *Curr. Opin. Cell Biol.*, 10: 614-9 (1998).
Durany et al., Studies on the expression of recombinant fuculose-1-phosphate aldolase in *E.coli*. *Process Biochem*, 39:1677-84 (2004).
Durham et. al., Alterations in insulin-like growth factor (IGF)-dependent IGF-binding protein-4 proteolysis in transformed osteoblastic cells. *Endocrinology*, 136(4):1374-80 (1995).
Ebara et. al., Mechanism for the action of bone morphogenetic proteins and regulation of their activity. *Spine*, 27(165):S10-5 (2002).
Eli Lilly Statement of Grounds of Appeal, Opposition to European Patent Application No. 1133558 B1, dated Sep. 28, 2009.
Eli Lilly, Biacore experiment comparison results, Setup assay to measure BMP binding to captured SOST, referenced on p. 41 of reference C193, dated Sep. 28, 2009.
Epstein et. al., Endocrine function in sclerosteosis. *S. Afr. Med. J.*, 55:1105-10 (1979).
European Patent Office Communication, Opposition to European Patent No. 1133558, dated Nov. 4, 2008.
European Patent Office, "Opinion of the Enlarged Board of Appeal dated Dec. 1992 G 1/92", available from [http://documents.epo.org/projects/babylon/eponet.nsf/0/907016FA57B46FD0C12572C8006CD2E2/$File/g920001.pdf], cited Jun. 15, 2011.
Expert Opinion from Dr. Catalina Lopez-Correa, submitted in Opposition to European Patent No. 1133558, dated Mar. 6, 2009.
Expert opinion of Professor Dr.-Ing Ulrich Vollrath. citation in Appeal of European Patent No. 1133558, dated Apr. 12, 2005.
Extract from Sigma Aldrich catalogue, cited in Opposition against European Patent No. 1721979 by Opponent: Laudens, dated Jun. 15, 2011.
Eyre et. al., Characterization of aromatase and 17β-hydroxysteroid dehydrogenase expression in rat osteoblastic cells. *J. Bone Miner. Res.*, 13(6): 996-1004 (1998).
Foster et. al., Establishment of interference in osteoblasts by an osteopetrosis-inducing Avian Leukosis virus. *Virology*, 205: 376-8 (1994).
Fouser et. al., Feedback regulation of collagen gene expression: A Trojan horse approach. *Proc. Natl. Acad. Sci. USA*, 88: 10158-62 (1991).

(56) References Cited

OTHER PUBLICATIONS

Frost et. al., On the rat model of human osteopenias and osteoporoses. *Bone and Mineral*, 18:227-36 (1992).
Fujiwara et. al., GenBank Sequence Database Accession No. D79813, Feb. 9, 1996.
Gardner et. al., Bone mineral density in sclerosteosis; Affected individuals and gene carriers. *J. Clin. Endocrinol. Metab.*, 90(12): 6392-5 (2005).
Gavarini et. al., Opposite effects of PSD-95 and MPP3 PDZ proteins on serotonin 5-hydroxytryptamine2C receptor desensitization and membrane stability. *Molec. Biol.*, 17: 4619-31 (2006).
Gazzerro et. al., Bone morphogenetic proteins induce the expression of noggin which limits their activity in cultured rat osteoblasts. *J. Clin. Invest.*, 102(12):2106-14 (1998).
Gazzerro et. al., Potential drug targets within bone morphogenetic protein signaling pathways. *Curr. Opin. Pharmacol.*, 7: 325-3 (2007).
Geissler et la., Male pseudohermaphroditism caused by mutations of testicular 17β-hydroxysteroid hehydrogenase 3. *Nat. Genetics*, 7: 34-9 (1994).
Gencic et. al., Conservative amino acid substitution in the myelin proteolipid protein of Jimpymsd mice. *J. Neurosci.*, 10(1):117-24 (1990).
Geysen et. al., Cognitive features of continuous antigenic determinants. *J. Molec. Recog.*, 1(1):32-41 (1988).
Gitelman et. al., Vgr-1/BMP-6 induces osteoblastic differentiation of pluripotential mesenchymal cells. *Cell Growth & Differentiation*, 6:827-36 (1995).
Glasky et. al., Stability of specific immunoglobulin secretion by EBV-transformed lymphoblastoid cells and human-murine heterohybridomas. *Hybridoma*, 8:377-89 (1989).
Glorieux et al., BPS804 Anti-Sclerostin Antibody in Adults with Moderate Osteogenesis Imperfecta: Results of a Randomized Phase 2a Trial, *J. Bone. Min Res.* 32(7):1496-1504 (2017).
Gowen et. al., Actions of recombinant human γ-interferon and tumor necrosis factor α on the proliferation and osteoblastic characteristics of human trabecular bone cells in vitro. *Arthritis Rheumatism*, 31(12): 1500-7 (1988).
Graner et. al., Splice variants of the *Drosophila* PS2 integrins differentially interact with RGD-containing fragments of the extracellular proteins tiggrin, Ten-m and D-laminin α2. *J. Biol. Chem.*, 273(29): 18235-41 (1998).
Green et al., Cytosolic pH regulation in osteoblasts. *J. Gen. Physiol.*, 95: 121-45 (1990).
Green et. al., Antigen-specific human monoclonal antibodies from mice engineered with human Ig heavy and light chain YACs. *Nat. Genet.*, 7:13 (1994).
Greene et. al., Screening Recombinant DNA Libraries. *Current Protocols in Molecular Biology*, Ch. 6(1) (1990).
Gribskov et. al., Profile analysis. *Meth. Enzym.*, 183:146-59 (1990).
Gribskov et. al., Profile analysis: Detection of distantly related proteins. *Proc. Nat. Acad. Sci. USA*, 84(13):4355-8 (1987).
Groeneveld et. al., Bone morphogenetic proteins in human bone regeneration. *Eur. J. Endocrinol.*, 142:9-21 (2000).
Gronthos et. al., Integrin expression and function on human osteoblast-like cells. *J. Bone Miner. Res.*, 12(8): 1189-97 (1997).
Groppe et. al., Structural basis of BMP signalling inhibition by the cystine knot protein noggin. *Nature*, 420:636-42 (2002).
Guinness-Hey, Increased trabecular bone mass in rats treated with human synthetic parathyroid hormone. *Metab. Bone Dis. Relat. Res.*, 5:177-81 (1984).
Harlow et. al., Antibodies: A Laboratory Manual, Cold Spring Harbor Laboratory, 141-157 (1988).
Harris, Processing of C-terminal lysine and arginine residues of proteins isolated from mammalian cell culture. *J. Chromatogr.*, 705:129-34 (1995).
Hart et. al., Crystal structure of the human TβR2 ectodomain-TGF-β3 complex. *Nat. Struc. Biol.*, 9(3):203-8 (2002).
Hay et. al., ATCC Cell Line and Hybridomas, American Type Culture Collection. 8th Ed., pp. 149, 258, 428 (1994).

He et. al., High-throughput dynamic light scattering method for measuring viscosity of concentrated protein solutions. *Anal. Biochem.*, 399(1): 141-3 (2010).
Heinecke et. al., Receptor oligomerization and beyond: A case study in bone morphogenetic proteins, *BMC Biol.*, 7: 59 (2009).
Hill et. al., Multiple extracellular signals promote osteoblast survival and apoptosis. *Endocrinology*, 138(9):3849-58 (1997).
Hillier et. al., EMBL Sequence Database Accession No. AA393939, May 19, 1997.
Hillier et. al., GenBank Sequence Database Accession No. AA393768, Apr. 24, 1997.
Hillier et. al., Generation and analysis of 280,000 human expressed sequence tags. *Genome Res.*, 6: 807-28(1996).
Hilliker et. al., Truncation of the amino terminus of PTH alters its anabolic activity on bone in vivo. *Bone*, 19(5): 469-77 (1996).
Hirschhorn, Letter to the editor: Dominance and homozygosity in man. *Am. J. Med. Genetics*, 18: 541 (1984).
Hock et. al., Perspective: Osteoblast apoptosis and bone turnover. *J. Bone Miner. Res.*, 16(6):975-84 (2001).
Hoffman et. al., BMP Signaling Pathways in Cartilage and Bone Formation, *Crit. Rev. Eukaryotic Gene Exp.*, 11(1-3):23-45 (2001).
Hoggard et al., Localization of leptin receptor mRNA splice variants in murine peripheral tissues by RT-PCR and in situ hybridization. *Biochem. Biophys. Res. Commun.*, 232: 383-7 (1997).
Hollinger et. al., Engineered antibody fragments and the rise of single domains. *Nat. Biotech.*, 23(9):1126-36 (2005).
Holm et. al., Protein folds and families: Sequence and structure alignments. *Nucl. Acid Res.*, 27(1):244-7 (1999).
Holt, et. al., Domain antibodies: Proteins for therapy. *Trends Biotechnol.*, 21(11):484-90 (2003).
Hoogenboom et. al., By-passing immunisation: Human antibodies from synthetic repertoires of germline VH gene segmens rearranged in vitro. *J. Molec. Biol.*, 227:381-8 (1992).
Hoogewerf et. al., Glycosaminoglycans mediate cell surface oligomerization of chemokines. *Biochemistry*, 36: 13570-8 (1997).
Horton et. al., Arg-Gly-Asp (RGD) peptides and the anti-vitronectin receptor antibody 23C6 inhibit dentine resorption and cell spreading by osteoclasts. *Exp. Cell Res.*, 195: 368-75 (1991).
Hsu et. al.,The Xenopus dorsalizing factor gremlin indentified a novel family of secreted proteins that antagonize BMP activities. *Molec. Cell*, 1:673-83 (1998).
Hufner et. al., Evidence for an osteoblast-activating factor in a patient with peripheral T-cell lymphoma and osteosclerosis. *Klin. Wochenscher.*, 67: 402-7 (1989).
Hugo et al., Functional Aspects of co-variant surface charges in an antibody fragment, Protein Science, 11:2697-705 (2002).
Hulley et. al., Inhibition of mitogen-activated protein kinase activity and proliferation of an early osteoblast cell line (MBA 15.4) by dexamethasone: Role of protein phosphatases. *Endocrinol.*, 139(5): 2423-31 (1998).
Huse et. al., Generation of a large combinatorial library of the immunoglobulin repertoire in phage lambda. *Science*, 246:1275-81 (1989).
Hwang et. al., Use of human germline genes in a CDR homoloy-based approach to antibody humanization. *Methods*, 36(1):35-42 (2005).
Ide et. al., GenBank Sequence Database Accession No. BAA19765, Feb. 7, 1999.
Ide et. al., GenBank Sequence Datacase Accession No. D89675, Feb. 7, 1999.
Iemura et. al., Direct binding of follistatin to a complex of bone-morphogenetic protein and its receptor inhibits ventral and epidermal cell fates in early Xenopus embryo. *Proc. Natl. Acad. Sci. USA*, 95:9337-42 (1998).
Innis et. al., Evolutionary trace analysis of TGF-B and related growth factors: Implications for stie-directed mutagenesis. *Protein Engineering*, 13(12):839-47 (2000).
Jakobovits et. al., Production of antigen-specific human antibodies from mice engineered with human heavy and light chain YACsa. *Ann. N.Y. Acad. Sci.*, 764:525-35 (1995).
Jee et al., Overview: Animal models of osteopenia and osteoporosis. *J. Musculoskel. Neuron. Interact.*, 1:193-207 (2001).

(56) References Cited

OTHER PUBLICATIONS

Jilka et. al., Increased bone formation by prevention of osteoblast apoptosis with parathyroid hormone. *J. Clin. Invest.*, 104:439-46 (1999).

Jilka et. al., Osteoblast programmed cell death (apoptosis): Modulation by growth factors and cytokines. *J. Bone Miner. Res.*, 13(5): 793-802 (1998).

Jones, Progress in protein structure predication. *Curr. Opin. Struct. Biol.*, 7(3):377-387 (1997).

Kabat et. al., Sequences of proteins of immunological interest, U.S. Department of Health and Human Services, *NIH*, USA (1987) (Table of Contents).

Kalu, The ovariectomized rat model of postmenopausal bone loss. *Bone and Mineral*, 15:175-92 (1991).

Kang et. al., Linkage of recognition and replication functions by assembling combinatorial antibody Fab libraries along phage surfaces. *Proc. Natl. Acad. Sci. USA*, 88:4363-6 (1991).

Katagiri et. al., The non-osteogenic mouse pluripotent cell line, C3H10T1/2, is induced to differentiate into osteoblastic cells by recombinant human bone morphogenetic protein-2. *Biochem. Biophys. Res. Comm.*, 172(1):295-9 (1990).

Kawabata et. al., Signal transduction by bone morphogenetic proteins. *Cytokine and Growth Factor Reviews*, 9(1):49-61 (1998).

Keller et. al. Molecular recognition of BMP-2 and BMP receptor IA. *Nat. Struct. Mol. Biol.*, 11(5):481-488 (2004).

Khalil, TGF-β: From latent to active. *Microbes and Infection*, 1(15):1255-63 (1999).

Khosla et. al., Concise review for primary-care physicians. Treatment pptions for osteoporosis. *Mayo Clin. Proc.*, 70:978-82 (1995).

Kirsch et. al., BMP-2 antagonists emerge from alterations in the low-affinity binding epitope for Receptor BMPR-II, *EMBO J.*, 19(13): 3314-24 (2000).

Kohler et. al., Continuous cultures of fused cells secreting antibody of predefined specificity. *Nature*, 256:495 (1975).

Koli et. al., Latency, activation, and binding proteins of TGF-. *Microscopy Res. Tech.*, 52:354-62 (2001).

Koreth et. al., Microsatellites and PCR genomic analysis. *J. Pathology*, 178:239-48 (1996).

Kramer et. al., The gapped duplex DNA approach to oligonucleotide-directed mutation construction. *Nuc. Acids Res.*, 12:9441 (1984).

Krause et. al., Distinct modes of inhibition by sclerostin on bone morphogenetic protein and Wnt signaling pathways. *J. Biol. Chem.*, 285(53): 41614-26 (2010).

Kunkel et. al., Rapid and efficient site-specific mutagenesis without phenoypic selection. *Meth. Enzymol.*, 154:367-82 (1987).

Kunkel, Rapid and efficient site-specific mutagenesis without phenotypic selection. *Proc. Natl. Acad. Sci. USA*, 82:488-92 (1985).

Kurahashi et. al., Regions of genomic instability on 22q11 and 11q23 as the etiology for the recurrent constitutional t (11;22). *Hum. Molec. Genet.*, 9: 1665-70 (2000).

Kusu et. al., Sclerostin is a novel secreted osteoclast-dervied bone morphogenetic protein antagonist with unique ligand specificity. *J. Biol. Chem.*, 278:24113-7 (2003).

Labat et. al., Retroviral expression in mononuclear blood cells isolated from a patient with osteopetrosis (Albers-Schonberg disease). *J. Bone Miner. Res.*, 5(5): 425-35 (1989).

Labat, A new approach to the study of the origin of genetic disease: Retroviral etiology of osteopetrosis. *Biomed. Pharmacother.*, 45: 23-7 (1991).

Lasic, Novel applications of liposomes. *Trends Biotechnol.*, 16(7):307-21 (1998).

Latham, The biochemical and cellular characterization of sclerostin, The causative gene for sclerostenosis. *Calcified Tissue International*, 70(4):244 (2002).

Lee and Kerns, LS/MS Applications in Drug Development, Mass Spectrometry Reviews, 18:187-279 (1999).

Leppert et. al., Benign familial neonatal epilepsy with mutations in two potassium channel genes. *Curr. Opin. Neurol.*, 12: 143-7 (1999).

Lewiecki et. al., Sclerostin monoclonal antibody therapy with AMG 785: A potential treatment for osteoporosis. *Exp. Opin. Biol. Ther.*, 11(1): 117-27 (2011).

Li et. al., Sclerostin binds to LRP5/6 and antagonizes canonical Wnt signaling. *J. Biol. Chem.*, 280: 19883-7 (2005).

Li et. al., Treatment with an anti-sclerostin antibody directly stimulates bone formation in a dose-dependent manner in ovariectomized rats with established osteopenia. *J. Bone Min. Res.*, 22(Suppl. S1): S65 (2007).

Lian et. al., Bone Formation: Osteoblast Lineage Cells, Growth Factors, Matrix Proteins, and the Mineralization Process, Primer on the Metabolic Bone Diseases and Disorders of Mineral Metabolism, 4th Edition, 14-29 (1999).

Lierop et. al., Van Buchem disease: Clinical, biochemical and densitometric features of patients and disease carriers. *J. Bone Miner. Res. Accepted Article* (2012).

Liu et. al., GenBank Sequence Database Accession No. U25110, Feb. 2, 1996.

Liu et. al., Human type II receptor for bone morphogenic proteins (BMPs): Extension of the two-kinase receptor model to the BMPs. *Molec. Cell. Biol.*, 15(7):3479-86 (1995).

Loftsson et al., Cyclodextrins in drug delivery. Expert Opin. Drug Deliv., 2(2):335-51 (2005).

Loftsson et al., Pharmaceutical Applications of Cyclodextrins. 1. Drug Solubilization and Stabilization. J Pharm Sci., 85(10):1017-25 (1996).

Lonberg et. al., Antigen-specific human antibodies from mice comprising four distinct genetic modifications. *Nature*, 368:856 (1994).

Loots et. al., Genomic deletion of a long-range bone enhancer misregulates sclerostin in Van Buchem disease. *Genome Res.*, 15: 928-35 (2005).

Low et. al., Mimicking somatic hypermutation: Affinity maturation of antibodies displayed on bacteriophage using a bacterial mutator strain. *J. Mol. Biol.*, 250:350-68 (1996).

Lowik et. al., Wnt signaling is involved in the inhibitory action of sclerostin on BMP-stimulated bone formation. *J. Musculoskeleton Neuronal Interact.* 6: 357 (2006).

Luckman et. al., Heterocycle-containing bisphosphonates cause apoptosis and inhibit bone resorption by preventing protein prenylation: Evidence from structure-activity relationships in J774 macrophages. *J. Bone Miner. Res.*, 13(11): 1668-78 (1998).

Luckman et. al., Nitrogen-containing bisphosphonates inhibit the mevalonate pathway and prevent post-translational prenylation of GTP-binding proteins, including Ras. *J. Bone Miner. Res.*, 13(4): 581-9 (1998).

Makrides, Strategies for achieving high-level expression of genes in *Escherichia coli. Microbiol Rev.*, 60(3):512-38 (1996).

Malone et. al., Bone anabolism achieved by reducing sclerostin bioavailability with an anti-sclerostin antibody. 37th International Sun Valley Workshop on Skeletal Tissue Biology. Aug. 5-8, 2007.

Mango et. al., Carboxy-terminal truncation activates glp-1 protein to specify vulval fates in Caenorhabditis elegans. *Lett. Nature*, 352: 811-15 (1991).

Margalit et. al., Comparative analysis of structurally defined herparin binding sequences reveals a distinct spatial distribution of basic residues. *J. Biol. Chem.*, 268 (26): 19228-31 (1993).

Margalit, Liposome-mediated drug targeting in topical and regional therapies. *Crit. Rev. Ther. Drug Carrier Syst.*, 12(2-3):233-61 (1995).

Marks et. al., By-passing immunization: Building high affinity human antibodies by chain shuffling. *Bio/Technology*, 10:779-83 (1992).

Matthews et. al., Adenovirus protein-protein interactions: Hexon and protein VI. *J. Gen. Virol.*, 75:3365-74 (1994).

Mayer et. al., Differentiation of osteogenetic cells: Systems and regulators, Z. Orthop., 130: 276-84 (1992)—Abstract Only.

McClung et. al., Inhibition of sclerostin with AMG 785 in postmenopausal women with low bone mineral density: Phase 2 trial results—Abstract presented at the 2012 meeting of the American Society for Bone and Mineral Reasearch (2012).

Memorandum C, Munich Diplomatic Conference, Sep. 1 to Oct. 6, 1973.

(56) References Cited

OTHER PUBLICATIONS

Minabe-Saegusa et. al., Genbank Sequence Database Accession No. AB011030. Jun. 23, 1998.
Minutes of EP2325199 Oral Proceedings dated Mar. 5, 2018.
Minutes of the oral proceedings before the opposition division for Opposition against European Patent No. 1721979, dated May 10, 2013.
Miyazono et. al., Divergence and convergence of TGF-β/BMP signaling. *J. Cell. Physiol.*, 187:265-76 (2001).
Miyazono et. al., TGF-β signaling by Smad proteins. *Adv. Immunology*, 75:115-57 (2000).
Morais et. al., In vitro biomineralization by osteoblast-like cells I. Retardation of tissue mineralization by metal salts. *Biomaterials*, 19: 13-21 (1998).
Mori et. al., A novel amino acid substitution a the receptor-binding site on the hemaglutinin of H3N2 influenza A viruses isolated from 6 cases with acute encephalopathy during 1997-1998 season in Tokyo. *Arch. Virol.*, 144: 147-55 (1999).
Morrison et. al., ATP is a potent stimulator of the activiation and formation of rodent osteoclasts. *J. Physiol.*, 511.2: 495-500 (1998).
Mosekilde et. al., Assessing bone quality—Animcal models in preclinincal osteoporosis research. *Bone*, 17 (4): 343S-52S (1995).
Moult, The current state of the art in protein structure predicion. *Curr. Opin. Biotech.*, 7(4):422-7 (1996).
Mullins et. al., Perspectives series: Molecular medicine in genetically engineered animals; Transgenesis in the rat and larger mammals. *J. Clin. Invest.*, 97(7):1557-60 (1996).
Muntoni et. al., A mutation in the dystrophin gene selectively affecting dystrophin expression in the heart. *J. Clin. Invest.*, 96: 693-9 (1995).
Nagaraja et. al., X chromosome map at 75-kb STS resolution, revealing extremes of recombination and GC content. *Genome Res.*, 7: 210-22 (1997).
Nakase et. al., Transient and localized expression of bone morphogenetic protein 4 messenger RNA during fracture healing. *J. Bone Miner. Res.*, 9(5):651-9 (1994).
Nelson, Positional cloning reaches maturity. *Curr. Opin. Genet. Devel.*, 5:298-303 (1995).
Nickel et. al., The crystal structure of the BMP-2: BMPR-1A complex and the generation of BMP-2 antagonists. *J. Bone Joint Surg.*, 83-A:S1-7-S1-14 (2001).
Nicolas et. al., An age-related decrease in the concentration of insulin-like growth factor binding protein-5 in human cortical bone. *Calcif. Tissue Int.*, 57:206-12 (1995).
Niessen, Liquid Chromatography—Mass Spectrometry, 3rd Ed. (2006 ).
Nifuji et. al., Coordinated expression of noggin and bone morphogenetic proteins (BMPs) during early skeletogenesi and induction of noggin expression by BMP-7. *J. Bone Miner. Res.*, 14(12):2057-66 (1999).
Nisonoff et. al., Separation of univalent fragments from the bivalent rabbit antibody molecule by reduction of disulfide bonds. *Arch. Biochem. Biophys.*, 89:230-44 (1960).
Niu et. al., Sclerostin inhibition leads to increased periosteal and endocortical bone formation as well as decreased cortical porosity in aged ovariectomized rats. *J. Bone Min. Res.*, 22(Suppl.S1) S65 (2007).
Nordsletten et. al., The neuronal regulation of fracture healing. *Acta Orthop Scand.*, 65(3): 299-304 (1994).
Notice of Opposition against European Patent No. 1133558, Opponent: Eli Lilly and Company, dated May 31, 2007.
Notice of Opposition against European Patent No. 1721979, Opponent: Eli Lilly & Company, dated Jun. 15, 2011.
Notice of Opposition against European Patent No. 1721979, Opponent: Laudens, dated Jun. 15, 2011.
Notice of Opposition against European Patent No. 1721979, Opponent: Novartis AG, dated Jun. 15, 2011.
Notice of Opposition against European Patent No. 2556841, dated Feb. 10, 2017.
Notice of Opposition to European Patent No. 1 133 558, dated May 29, 2007.
Nygren et. al., Scaffolds for engineering novel binding sites in proteins. *Curr. Opin. Struct. Biol.*, 7:463-9 (1997).
Observations of Opponent: Laudens in response to summons to oral proceedings in Opposition against European Patent No. 1721979, dated Feb. 25, 2013.
Oelgeschlager et. al., The evolutionarily conserved BMP-binding protein twisted gastrulation promotes BMP signalling. *Nature*, 405:757-63 (2000).
OMIM #607625, Niemann-pick disease, type C2 (2007).
Ominsky, et. al., Sclerostin monoclonal antibody treatment increases bone strength in aged osteopenic ovariectomozed rats. *J. Bone Min. Res.*, 21 (1): S44 PRES1161 (2006). Abstract.
Opposition Decision for Opposition against European Patent No. 1721979, dated Aug. 2, 2013.
Opposition Statement of May 20, 2007 filed by Opponent 2 (Eli Lilly) against European Patent No. 1133558.
Oreffo et. al., Human bone marrow osteoprogenitors express estrogen receptor-alpha and bone morphogenetic proteins 2 and 4 mRNA during osteoblastic differentiation. *J. Cell. Biochem.*, 75:382-92 (1999).
Orriss et al., Purinergic signaling and bone remodeling. *Curr. Opin. Pharmacol.*, 10:322-30 (2010).
Oshima et. al., TGF-β receoptor type II deficiency results in defects of yolk Sac hematopoiesis and vasculogenesis. *Dev. Biol.*, 179:297-302 (1996).
Otzen et al., Structural basis for cyclodextrins' suppression of human growth hormone aggregation. *Protein Sci.*, 11(7):1779-87 (2002).
Padhi et. al., Anti-sclerostin antibody increases markers of bone formation in healthy postmenopausal women. *J. Bone Min. Res.*, 22: S37 (2007).
Padhi et. al., OC35—Effects of anti-sclerostin monoclonal antibody in healthy postmenopausal women. *Osteoporosis Int.*, 19: Suppl. 1: S19 (2008).
Padlan et. al., Structure of an antibody-antigen complex; Crystal structure of the HyHEL-10 Feb-lysozyme complex. *Proc. Natl. Acad. Sci. USA*, 86:5938-42 (1989).
Palokangas et. al., Endocytic pathway from the basal plasma membrane to the ruffled border membrane in bone-resorbing osteoclasts. *J. Cell Sci.*, 110:1767-80 (1997).
Pandey et. al., Nucleotide sequence database: A gold mine for biologists. *TIBS.*, 24: 276-80 (1999).
Papapoulos et. al., Targeting sclerostin as potential treatment of osteoporosis. *Ann. Rheum. Dis.*, 70(Suppl. 1): I119-22 (2011).
Patel et. al., Current and potential future drug treatments for osteoporosis. *Ann. Rheumatic Dis.*, 55:700-14 (1996).
Patentee's Oct. 5, 2012 Submission in EP 2325199.
Patten et. al., Applications of DNA shuffling to pharmaceuticals and vaccines. *Curr. Opin. Biotechnol.*, 8:724-33 (1997).
Pearson et. al., Effective protein sequence comparison. Chapter 15, pp. 227-258 (1996).
Piao et. al., The proximal promoter region of the gene encoding human 17β-hydroxysteroid dehydrogenase type 1 contains GATA, AP-2, and Sp1 response elements: Analysis of promotor function in choriocarcinoma cells. *Endrocrinol.*, 138(8): 3417-25 (1997).
Piccolo et. al., The head inducer Cerberus is a multifunctional antagonist of nodal, BMP and Wnt signals. *Nature*, 397: 707-10 (1999).
Piek et. al., Specificity, diversity, and regulation of TGF-β superfamily signaling. *FASEB J.*, 13:2105-24 (1999).
Pietromonaco et. al., Protein kinase C-⊖ phosphorylation of moesin in the actin-binding sequence. *J. Biol. Chem.*, 273:7594-603 (1998).
Pignatti et. al., Tracking disease genes by reverse genetics. *J. Psychiar. Res.*, 26(4):287-98 (1992).
Pittenger et. al., Multilineage potential of adult human mesenchymal stem cells. *Science*, 284:143-7 (1999).
Pluckthun et. al., Expression of functional anitbody Fv and Fab fragments in *Escherichia coli. Meth. Enzymol.*, 178:497-515 (1989).

(56) References Cited

OTHER PUBLICATIONS

Pockwinse et. al., Expression of cell growth and bone specific genes at single cell resolution during development of bone tissue-like organization in primary osteoblast cultures. *J. Cell. Biol.*, 49:310-23 (1992).
Poole et. al., Sclerostin is a delayed secreted product of osteocytes that inhibit bone formation. *FESEB J.*, 19: 1842-4 (2005).
Porter, The hydrolysis of rabbit γ-globulin and antibodies with crystalline papain. *Biochem. J.*, 73:119-26 (1959).
Proprietor's Response to Opponent's Statement of Grounds of Appeal, European Patent No. 1133558, dated Apr. 15, 2010.
Proprietor's Response to Oppositions against European Patent No. 1721979, UCB Pharma S.A., dated Feb. 20, 2012.
Proprietor's Written submission in preparation for oral proceedings in Opposition against European Patent No. 1721979, Proprietor: UCB Pharma S.A., dated Feb. 25, 2013.
Quintanar-Guerrero et. al., Preparation techniques and mechanisms of formation of biodegradable nanoparticles from preformed polymers. *Drug Dev. Ind. Pharm.*, 24(12):1113-28 (1998).
Rachner et. al., Osteoporosis: Now and the future. *Lancet*, 377(9773): 1276-87 (2011).
Rawadi et. al., BMP-2 controls alkaline phosphatase expression and osteoblast mineralization by a Wnt autocrine loop. *J. Bone Min. Res.*, 18: 1842-53 (2003).
Reb, Antikorpergegen sclerostin, *Medical Tribune*, 39:12 (2007).
Reddi et. al., The *Escherichia coli* chaperonin 60 (groEL) is a potent stimulator of osteoclast formation. *J. Bone Miner. Res.*, 13(8): 1260-6 (1998).
Reddi, Interplay between bone morphogenetic proteins and cognate binding proteins in bone and cartilage development: Noggin, chordin and DAN. *Arthritis Res.*, 3(1):1-5 (2000).
Reid, Targeting Sclerostin in Postmenopausal Osteoporosis: Focus on Romosozumab and Blososumab, *BioDrugs* 31:289-97(2017).
Response to Proprietor's brief of Apr. 15, 2010, European Patent Opposition, EP-1133558 B1, dated Mar. 18, 2011.
Reverberi et al., Factors affecting the antigen-antbody reaction, *Blood Transfus*, 5:227-240 (2007).
Riggs, Overview of osteoporosis. *West J. Med.*, 154:63-77 (1991).
RnD Systems catalogue excerpt, cited in Opposition against European Patent No. 1721979 by Opponent: Novartis AG dated Jun. 15, 2011.
Robb et al., Atmospheric Pressure Photoionization: An Ionization Method for Liquid Chromatogreapy—Mass Spectrometry, Anal. Chem. 72:3653-59 (40000).
Roberts et. al., Essential functional interactions of SAFA, a *Saccharomyces cerevisiae* complex of Spt, Ada, and Gcn5 proteins, with the Snf/Swi and Srb/Mediator complexes. *Genetics*, 147: 451-65 (1997).
Robinson et. al., The sclerostin antibody project. *Hum. Antibodies*, 16: 36 (2007).
Roitt et la., Roitt's Essential Immunology, 9th Edition, pp. 90-91 (1997).
Rosenzweig et. al., Cloning and characterization of a human type II receptor for bone morphogenetic proteins. *Proc. Natl. Acad. Sci. USA*, 92:7632-7636 (1995).
Rosenzweig et. al., GenBank Sequence Database Accession No. CAA88759, Oct. 7, 2008.
Rosenzweig et. al., GenBank Sequence Database Accession No. Z48923, Oct. 7, 2008.
Rudikoff, et. al., Single amino acid substitution altering antigen-binding specificity. *Proc. Natl. Acad. Sci. USA*, 79:1979-83 (1982).
Ruppert et. al., Human bone morphogenetic protein 2 contains a heparin-binding site which modifies its biological activity. *Eur. J. Biochem.*, 237: 295-302 (1996).
Sada et. al., Adsorption equilibirum in immuno-affinity chromatography with polyclonal and monoclonal antibodies. *Biotechnol. Bioengin.*, 28 (1986). Abstract.
Sali et. al., Comparative protein modeling by satisfaction of spatial restraints. *J. Mol. Biol.*, 234(3):779-815 (1993).

Sambrook et. al., Synthetic oligonucleotide probes, molecular cloning—A Laboratory Manual, Ch. 11:11.1-11.19 and 11.58-11.61 (1989).
Sanger et. al., DNA sequencing with chain-terminating inhibitors. *Proc. Natl. Acad. Sci. USA*, 74:5463-7 (1997).
Sastry et. al., Cloning of the immunological repertoire in *Escherichia coli* for generation of monoclonal catalytic antibodies: Construction of a heavy chain variable region-specific cDNA library. *Proc. Natl. Acad. Sci. USA*, 86:5728-32 (1989).
Scatchard et. al., The attractions of proteins for small molecules and ions. *Ann. N.Y. Acad. Sci.*, 51:660-72 (1949).
Scheufler et. al., Crystal structure of human bone morphogenetic protein-2 at 2.7 A resolution. *J. Mol. Biol.*, 287(1):101-15 (1999).
Schlebusch et. al., Production of a single-chain fragment of the murine anti-idiotypic antibody ACA125 as phage-displayed and soluble antibody by recombinant phage antibody technique. *Hybridoma*, 16:47-52 (1997).
Schlunegger et. al., Refined crystal structure of human transforming growth factor β2 at 1.95 A Resolution. *J. Mol. Biol.*, 231(2):445-458 (1993).
Schmidt et. al., Retrovirus-induced osteopetrosis in mice: Effects of viral infection on osteogenic differentiation in skeletoblast cell cultures. *Am. J. Pathol.*, 129(3): 503-10 (1987).
Schmitt et. al., Bone morphogenetic proteins: An update on basic biology and clinical relevance. *J. Orth. Res.*, 17:269-78 (1999).
Schwappacher et. al., NCBI Sequence Database Accession No. NM_001204, Aug. 16, 2009.
Scully et. al., BRCA1 is a component of the RNA polymerase II holoenzyme. *Proc. Natl. Acad. Sci. USA*, 94: 5605-10 (1997).
Second declaration of Martyn Robinson, citation in Appeal, European Patent No. 1133558, dated Apr. 15, 2010.
Serra et. al., Expression of a truncated, kinase-defective TGF-β type II receceptor in mouse skeletal tissue promotes terminal chondrocyte differentiation and osteoarthritis. *J. Cell. Biol.*, 139(2):541-52 (1997).
Sigmund, Viewpoint: Are studies in genetically altered mice out of control? *Arterioscler. Thromb. Vasc. Biol.*, 20:1425-9 (2000).
Silverman et. al., Sclerostin, *J. Osteoporosis*, 2010: 1-3 (2010).
Sippl et. al., Threading thrills and threats. *Structure*, 4(1):15-19 (1996).
Siris, Clinical Review: Paget's disease of bone. *J. Bone Miner. Res.*, 13(7): 1061-5 (1998).
Sivakumar et. al., New insights into extracellular matrix assembly and reorganization from dynamic imaging of extracellular matrix proteins in living osteoblasts. *J. Cell. Sci.*, 119(7):1350-60 (2006).
Skiple Skjerpen et. al., Binding of FGF-1 variants to protein kinase CK2 correlates with mitogenicity. *EMBO J.*, 21(15): 4058-69 (2002).
Slater et. al., Involvement of platelets in stimulating osteogenic activity. *J. Orthopaedic Res.*, 13: 655-63 (1995).
Smith et. al., Glucocorticoids inhibit development stage-specific osteoblast cell cycle. *J. Biol. Chem.*, 275:19992-20001 (2000).
Smith, TGF β inhibitors, new and unexpected requirements in vertebrate development. *TIG*, 15(1):3-5 (1999).
Sohocki et. al., A range of clinical phenotypes associated with mutations in CRX, a photoreceptor transcription-factor gene. *Am. J. Hum. Genet.*, 63: 1307-15 (1998).
Spranger, International classification of osteochondrodysplasias, *Eur. J. Pediatr.*, 151: 407-15 (1992).
Staehling-Hampton et. al., A 52-kb delection in the SOST-MEOX1 intergenic region on 17q12-q21 is associated with van Buchem disease in the Dutch population. *Am. J. Med. Gen.*, 110: 144-52 (2002).
Stanley et. al., DAN is a secreted glycopeotein related to Xenopus cerberus. *Mech. Dev.*, 77: 173-84 (1998).
Statement of Grounds of Appeal to Decision of Opposition against European Patent No. 1133558, dated Sep. 28, 2009.
Stenmark et. al., Distinct structural elements of rab5 define its functional specificity. *EMBO J.*, 13(3): 575-83 (1994).
Strachan et. al. (Eds.), Diagram from text book entitled Human Molecular Genetics, 2nd Edition (1999).
Strachan et. al. (Eds.), Human Molecular Genetics, 1st Edition, p. 420 (1996).
Strachan et. al., (Eds.), Human Molecular Genetics, 2nd Edition, Figure 15.4 (1999).

(56) References Cited

OTHER PUBLICATIONS

Submission in response to oral proceedings in Opposition against European Patent No. 1721979, Opponent: Eli Lilly, dated Apr. 24, 2013.
Sudo et. al., In vitro differentiation and calcification in a new clonal osteogenic cell line derived from newborn mouse calvaria. *J. Cell Biol.*, 96:191-8 (1983).
Summons to attend oral proceedings for Opposition against European Patent No. 1133558, dated Nov. 4, 2008.
Summons to attend oral proceedings in Opposition against European Patent No. 1721979, dated Nov. 12, 2012.
Summons to attend oral proceedings regarding opposition against European Patent No. 2556841, dated Aug. 29, 2017.
Sutherland et. al., Sclerostin romotes the apoptosis of human osteoblastic cells: A novel regulation of bone formation. *Bone*, 35:828-35 (2004).
Suzawa et. al., Extracellular matrix-associated bone morphogenetic proteins are essential for differentiation of murine osteoblastic cells in vitro. *Endocrinology*, 140:2125-33 (1999).
Sverdlov et. al., Perpetually mobile footprints of ancient infections in human genome. *FEBS Lett.*, 428: 1-6 (1998).
Sylatron label, cited in Opposition against European Patent No. 1721979 by Opponent: Novartis AG, dated Jun. 15, 2011.
Szejtli, Past, present and future of cyclodextrin research. Pure Appl. Chem., 76(10):1825-45 (2004).
Takakura, Drug delivery systems in gene therapy. *Nippon Rinsho*, 56(3):691-5 (1998) (Abstract Only).
Takeda et. al., GenBank Sequence Database Accession No. AAB33865, May 27, 1995.
Takeda et. al., GenBank Sequence Database Accession No. D38082, dated Dec. 27, 2006.
Takeda et. al., GenBank Sequence Database Accession No. S75359, May 27, 1995.
Takeda et. al., NCBI Sequence Database Accession No. NM_030849, Feb. 11, 2009.
Takeda, Expression of serine/threonine kinase receptors during ectopic bone formation induced by bone morphogenetic protein (BMP). *Kokubyo Gakkai Zasshi*, 61(4):512-26 (1994).
Tam et. al., TGF-β receptor expression on human keratinocytes: A 150 kDa GPI-anchored TGF-β1 binding protein forms a heteromeric complex with type I and type II receptors. *J. Cellular Biochem.*, 70:573-56 (1998).
Taylor et. al., Human immunoglobulin transgenes undergo rearrangement, somatic mutation and class switching in mice that lack endogenous IgM. *Int. Immun.*, 6:579 (1994).
Terpe, Overview of bacterial expression systems for heterologous protein production: from molecular and biochemical fundamentals to commercial systems. *Appl. Microbiol. Biotechnol.*, 72(2):211-22 (2006).
The Merck Manual-Second Home Edition, Ch. 61:1-3 (2005).
Thompson et. al., Affinity maturation of a high-affinity human monoclonal antibody against the third hypervariable loop of human immunodeficiency virus: Use of phage display to improve affinity and broaden strain reactivity. *J. Mol. Biol.*, 256:7-88 (1996).
Thornton et. al., Prediction of progress at last. *Nature*, 354:105-6 (1991).
Tjaderhane et. al., A high sucrose diet decreases the mechanical strength of bones in growing rats. *J. Nutr.*, 128: 1807-10 (1998).
Tuncay et. al., Oxygen tension regulates osteoblast function. *Am. J. Orthod. Dentofac. Orthop.*, 105:457-63 (1994).
UCB and Amgen announce positive phase 2 results of CDP7851/AMG785 in patients with post menopausal osteoporosis (PMO), dated Apr. 21, 2011—Citation in Opposition against European Patent No. 1721979.
Uitterlinden et. al., Relation of alleles of the collagen type Iα1 gene to bone density and the risk of osteoporotic fractures in postmenopausal women. *New Engl. J. Med.*, 338: 1016-21 (1998).
Utting et al., Hypoxia stimulates osteoclast formation from human peripheral blood. *Cell Biochem. Funct.*, 28:374-80 (2010).

Valero et. al., Quaternary structure of casein kinase 2. *J. Biol. Chem.*, 27(14): 8345-52 (1995).
van Bezooijen et. al., Sclerostin is an osteocyte-expressed negative regulator of bone formation, but not a classical BMP antagonist. *J. Exp. Med.*, 199: 805-14 (2004).
van Bezooijen et. al., SOST/sclerostin, an osteocyte-derived negative regulator of bone formation, *Cytokine Growth Factor Rev.*, 16: 319-27 (2005).
van Bezooijen et. al., Wnt but not BMP signaling is involved in the inhibitory action of sclerostin on BMP-stimulated bone formation. *J. Bone. Miner. Res.*, 22:19-28 (2007).
Van Hul et. al., Van Buchem Disease (hyperostosis corticalis generalisata) maps to chromosome 17q12-a21. *Am. J. Hum. Genet.*, 2:391-9 (1998).
Vanier et. al., Recent advances in elucidating Niemann-Pick C disease. *Brain Pathol.*, 8: 163-74 (1998).
Veverka et. al., Characterization of the structural features and interactions of sclerostin. *J. Biol. Chem.*, 284(16): 10890-900 (2009).
Viter et. al., Analysis of antigenic structure of potato virus M Ukrainian strains. *Biopolimery I Kletka, Naukova Dumka, Kiev K, UK*, 16: 312-9 (2000).
Von Bubnoff et. al., Intracellular BMP signaling regulation in vertebrates: Pathway or network? *Dev. Biol.*, 239:1-14 (2001).
Wall, Transgenic livestock: Progress and prospects for the future. *Theriogenology*, 45:57-68 (1996).
Wang et. al., IFP 35 forms complexes with B-ATF, a member of the AP1 family of transcription factors. Biochem. Biophys. *Res. Commun.*, 229: 316-22 (1996).
Wang, Bone morphogenetic proteins (BMPs): Therapeutic potential in healing bony defects. *TIBTECH*, 11:379-83 (1993).
Warmington et al., Presentation 1217 at American Society for bone and Mineral Research annual meeting Seattle (Oct. 2004).
Warmington et al., Oasis Online Abstract Submission and Invitation System—Program Planner, "Sclerostin Monoclonal Antibody Treatment of Osteoporotic Rats Completely Reverses One Year of Ovariectomy-Induced Systemic Bone Loss" downloaded Nov. 23, 2015.
Warmington et. al., Sclerostin antagonism in adult rodents, via monoclonal antibody mediated blockade, increases bone mineral density and implicates sclerostia as a key regulator of bone mass during adulthood. *J. Bone Min. Res.*, 19:S56-7 (2004).
Warmington et. al., Sclerostin monoclonal antibody treatment of osteoporotic rats completely reverses one year of overiectomy-induced systemic bone loss, *J. Bone Min. Res.*, 20:S22 (2005).
Winkler et. al., Noggin and sclerostin bone morphogenetic protein antagonists form a mutually inhibitory complex. *J. Biol. Chem.*, 279(35): 36296-8 (2004).
Winkler et. al., Osteocyte control of bone formation via sclerostin, a novel BMP antagonist. *EMBO J.* 22: 6267-76 (2003).
Winkler et. al., Sclerostin inhibition of Wnt-3a-induced C3H10T1/2 cell differentiation is indirect and mediated by bone morphogenetic proteins. *J. Biol. Chem.* 280: 2498-502 (2005).
Winter et. al., Making antibodies by phase display technology. *Annu. Rev. Immunol.*, 12:433-55 (1994).
Wolff et. al., Monoclonal antibody homodimers: Enhanced antitumor activity in nude mice. Cancer Res., 53:2560-5 (1993).
Wollenberger et. al. (Eds.), Analytische Biochemie, Chapter 3, pp. 47-49 (2003).
Written Decision to Revoke EP 2556841, dated Jul. 19, 2018.
Written submission—Observation by a Third Party According to Art. 115 EPC, Opposition to European Patent No. 1133558, dated Nov. 25, 2008.
Written submission in response to summons to oral proceedings in Opposition against European Patent No. 1721979, Opponent: Norvartis AG, dated Feb. 25, 2013.
Written submission in response to summons to oral proceedings in Opposition against European Patent No. 1721979, Opponent: Eli Lilly Company, dated Feb. 25, 2013.
Written submission of Eli Lilly & Company to European Patent Office, Opposition to European Patent No. 1133558, dated May 29, 2007.
Written Submission of Eli Lilly & Company, Opposition to European Patent No. 1133558, dated Mar. 9, 2009.

(56) References Cited

OTHER PUBLICATIONS

Written Submission of Opponent in response to summons to oral proceedings in Opposition against European Patent No. 2556841, dated Feb. 16, 2018.
Written submission of UCB S.A., Proprietor's Preliminary Response to the Opponent's submission of Mar. 9, 2009, Opposition to European Patent No. 1133558, dated Mar. 20, 2009.
Written submission of UCB S.A., Proprietor's Response to Opposition against European Patent No. 1133558, dated Mar. 14, 2008.
Written Submission, Proprietor's reply to the Notice of Opposition against European Patent No. 2556841, dated Jul. 25, 2017.
Yanagita et. al., USAG-1: A bone morphogenetic protein antagonist abundantly expressed in the kidney. *Biochem. Biophys. Res. Comm.*, 316: 490-550 (2004).
Yang et. al., CDR walking mutagenesis for the affinity maturation of a potent human Anti-HIV-1 antibody into the picomolar range. *J. Mol. Biol.*, 254:392-403 (1995).
Yates et. al., Inhibition of bone resorption by inorganic phosphate in mediated by both reduced osteoclast formation and decreased activity of mature osteoclasts. *J. Bone Miner. Res.*, 6(5): 476-8 (1990).
Yerges et. al., NCBI Sequence Database Accession No. NM_001203, Jul. 12, 2009.
Yerges et. al., NCBI Sequence Database Accession No. NP_001194, Jul. 12, 2009.
Yoshida et. al., Osteoinduction capability of recombinant human bone morphogenetic protein-2 in intramuscular and subcutaneous sites: An experimental study. *J. Cranio-Maxillofac. Surg.*, 26: 112-5 (1998).
Zambaux et. al., Influence of experimental parameters on the characteristics of poly(lactic acid) nanoparticles prepared by a double emulsion method. *J. Controlled Rel.*, 50(1-3):31-40 (1998).
Zhang et. al., Humanization of an anti-human TNF-β antibody by variable region resurfacing with the aid of molecular modeling. *Molec. Immunol.*, 42(12):1445-51 (2005).
Zimmerman et. al., The spemann organizer signal noggin binds and inactives bone morphogenetic protein 4. *Cell*, 86(4):599-606 (1996).
Zlotogora et. al., Dominance and homozygosity, *Am. J. Med. Genet.*, 68: 412-6 (1997).
zur Muhlen et. al., Solid lipid nanoparticles (SLN) for controlled drug delivery—Drug release and release mechanism. *Eur. J. Pharm. Biopharm.*, 45(2):149-55 (1998).
Lilyestrom et al., "Monoclonal Antibdy Self-Association, Cluster Information, and Rheology at High Concentrations", The Journal of Physical Chemistry, 117: 6373-6384, Jan. 24, 2013.
Binbaji et al., "Intermolecular Interactions and the Viscosity of Highly Concentrated Monoclonal Antibody Solutions", Parm Res, 32:3 |02-3109, Apr. 2, 2015.
Wang et al., "Viscosity-Lowering Effect of Amino Acids and Salts on Highly Concentrated Solutions of Two IgG1 Monoclonal Antibodies", Molucular Pharmaceutics, 12: 4478-4487, Nov. 3, 2015.
He et al., "Screening of Monoclonal Antibody Formulations Based on High-Throughout Thermostability and Viscosity Measurements: Design of Experiment and Statistical Analysis", Journal of Pharmaceutical Sciences, vol. 100 No. 4, pp. 1330-1340, Nov. 2, 2010.
Taneja et al., "Increased thermal stability of proteins in the presence of amino acids", Biochem. J. 303: 147-153, May 9, 1994.
Chari et al., "Long-and Short-Range Electrostatic Interactions Affect the Rheology of Highly Concentrated Antibody Solutions", Pharmaceutical Research, vol. 26, No. 12, pp. 2607-2618, Dec. 12, 2009.
Roberts et al., "Role of Anisotropic Interactions for Proteins and Patchy Nanoparticles", The Journal of Physical Chemistry B, 118: 12599-12611, Oct. 10, 2014.
Forney-Stevens et al., Addition of Amino Acids to Further Stabilize Lyophilized Sucrose-Based Protein Formulations: I. Screening of 15 Amino Acids in Two Model Proteins, Journal of Pharmaceutical Sciences, 101: 697-704, Sep. 28, 2015.
Donard S. Dwyer, "Chemical Properties of Amino Acids", Wiley Encyclopedia of Chemical Biology ©, John Wiley & Sons, Inc., pp. 1-12, May 2008.

\* cited by examiner

Fig. 1

SEQ ID NO: 11

```
  1  M Q I D V R M T Q S P S S L S A S L G D R V T I T C R A S Q S I S S Y L N W Y Q Q K
 58  P G K A P K L L I Y A A S S L Q S G V P S R F S G S G S G T D F T L T I S S L Q P E
115  D F A T Y Y C Q Q S Y S T P L T F G Q G T K V E I K R T V A A P S V F I F P P S D E
172  Q L K S G T A S V V C L L N N F Y P R E A K V Q W K V D N A L Q S G N S Q E S V T E
```

(Sequence as shown in figure, positions 1–210)

Fig. 2

SEQ ID NO:12

Fig. 2 cont.

SEQ ID NO:12 cont.

| 229 | 248 | 267 | 286 | 305 | 324 | 343 | 362 | 381 | 400 | 419 | 438 |
|---|---|---|---|---|---|---|---|---|---|---|---|
| Cys C | Lys K | Asp D | Val V | Val V | Lys K | Gly G | Lys K | Val V | Leu L | Trp W | Tyr Y |
| Pro P | Pro P | Val V | His H | Ser S | Val V | Gln Q | Asn N | Glu E | Asp D | Gln Q | Thr T |
| Pro P | Lys K | Ser S | Asn N | Val V | Ser S | Pro P | Gln Q | Trp W | Ser S | Gln Q | Gln Q |
| Cys C | Asp D | His H | Ala A | Leu L | Asn N | Arg R | Val V | Glu E | Asp D | Gly G | Lys K |
| Pro P | Thr T | Glu E | Lys K | Thr T | Lys K | Glu E | Ser S | Ser S | Gly G | Asn N | Ser S |
| Ala A | Leu L | Asp D | Thr T | Val V | Gly G | Pro P | Leu L | Asn N | Ser S | Val V | Leu L |
| Pro P | Met M | Pro P | Lys K | Val V | Leu L | Gln Q | Thr T | Gly G | Phe F | Phe F | Ser S |
| Pro P | Ile I | Glu E | Pro P | His H | Pro P | Val V | Cys C | Gln Q | Phe F | Ser S | Leu L |
| Val V | Ser S | Val V | Arg R | Gln Q | Ala A | Tyr Y | Leu L | Pro P | Leu L | Cys C | Ser S |
| Ala A | Arg R | Gln Q | Glu E | Asp D | Pro P | Thr T | Val V | Glu E | Tyr Y | Ser S | Pro P |
| Gly G | Thr T | Phe F | Glu E | Trp W | Ile I | Leu L | Lys K | Asn N | Ser S | Val V | Gly G |
| Pro P | Pro P | Asn N | Gln Q | Leu L | Glu E | Pro P | Gly G | Asn N | Lys K | Met M | Lys K |
| Ser S | Glu E | Trp W | Phe F | Asn N | Lys K | Pro P | Phe F | Tyr Y | Leu L | His H | |
| Val V | Val V | Tyr Y | Asn* N | Gly G | Thr T | Ser S | Tyr Y | Lys K | Thr T | Glu E | |
| Phe F | Thr T | Val V | Ser S | Lys K | Ile I | Arg R | Pro P | Thr T | Val V | Ala A | |
| Leu L | Cys C | Asp D | Thr T | Glu E | Ser S | Glu E | Ser S | Thr T | Asp D | Leu L | |
| Phe F | Val V | Gly G | Phe F | Tyr Y | Lys K | Glu E | Asp D | Pro P | Lys K | His H | |
| Pro P | Val V | Val V | Arg R | Lys K | Thr T | Met M | Ile I | Pro P | Ser S | Asn N | |
| Pro P | Val V | Glu E | Val V | Cys C | Lys K | Thr T | Ala A | Met M | Arg R | His H | |

PHARMACEUTICAL FORMULATIONS

CROSS-REFERENCE TO RELATED APPLICATIONS

This application is a National Stage Application of International Patent Application No. PCT/EP2017/055594, filed Mar. 9, 2017, which claims priority from Great Britain Patent Application No. 1604124.6, filed Mar. 10, 2016.

FIELD OF THE INVENTION

The present invention belongs to the field of pharmaceutical formulations. More specifically, it relates to a pharmaceutical formulation comprising an antibody, cyclodextrin and methionine.

BACKGROUND OF THE INVENTION

Antibodies are large and complex molecules and are inherently chemically and physically instable when stored over a period of time at high concentration. Typical chemical instability may result in deamidation, hydrolysis, oxidation, beta-elimination or disulfide exchanges. Physical instability can result in denaturation, aggregation or precipitation.

Antibodies can be formulated in freeze-dried, i.e. lyophilized form for reconstitution in a solvent shortly before administration. Freeze-dried formulations of antibodies tend to be more stable than liquid water-based formulation as water is either a reactant or facilitates the transfer of reactants and is thus critical to chemical degradation and protein instability. Despite being less stable, interest has recently focused on liquid formulations of antibodies. These formulations are easier and more convenient for the patient and the healthcare professional to handle and administer in comparison to freeze-dried formulations. Liquid formulations do not need to be reconstituted and can be administered with minimal preparation. However, the stabilization of proteins in liquid formulations to avoid or minimize aggregation, precipitation or degradation remains a particular challenge. Aggregation, with the formation of insoluble matter or precipitate, is a particular problem. This may cause various problems. Firstly aggregate formation may result in the antibody being less or no longer active; aggregate may provoke undesired and unexpected immunological reactions upon administration and finally aggregates may prevent proper administration of the pharmaceutical formulation e.g. by blocking syringes or pumps. These problems are even more evident in liquid formulations for subcutaneous administration where antibodies are present at high concentrations in much smaller volumes than intravenous infusions.

A typical strategy for preventing aggregation is to add stabilizers to the antibody formulation. Commonly used stabilizers include sugars, salts, free amino acids, polyols, polyethylene glycols (PEGs), and other polymers, such as polysorbates or poloxamers that may reduce protein-protein interactions.

Cyclodextrins (sometimes called cycloamyloses) are a family of compounds made up of sugar molecules bound together in a ring (cyclic oligosaccharides). Cyclodextrins are produced from starch by means of enzymatic conversion. They are considered safe and are widely used in food, pharmaceutical drug delivery, and chemical industries, as well as agriculture and environmental engineering. Cyclodextrins are composed of 5 or more α-D-glucopyranoside units linked 1→4, as in amylose. Typical cyclodextrins contain 6 (alpha-cyclodextrin), 7 (beta-cyclodextrin) or 8 (gamma-cyclodextrin) glucose monomers units in a ring, creating a cone shape where the interior is hydrophobic and the exterior is hydrophilic. The hydrophobic cavity provides an environment into which non-polar compounds, e.g. non-polar amino acids can be included and form complexes.

WO2010057107 describes using cyclodextrins (CDs) for reducing aggregation under physiological conditions. Furthermore, cyclodextrins and its derivatives have been used as solubilizers for poorly water soluble drugs. Currently available drug products that contain cyclodextrin in liquid formulations include Sporanox™ (Janssen, Belgium), Prostavasin (Ono, Japan; Schwarz, Germany), Prostandin 500 (Ono, Japan), Geodon™ (Pfizer, USA), VFEND™ (Pfizer, USA), MitoExtra Mitozytrex™ (Novartis, Switzerland), and Voltaren Optha™ (Novartis, Switzerland) (Szejtli J., Pure Appl. Chem. 76:1825-1845 (2004); Loftsson T. et al, Expert Opin. Drug Deliv. 2, 335-351 (2005)). Most of these formulations are for small molecule compounds. Maximum benefit is usually obtained at low cyclodextrin concentrations, and the benefits are often only partially concentration dependent. For example, aggregation of IL-2 was optimally inhibited by 0.5% HP-beta-cyclodextrin. (Loftsson T. and Brewster M. E., J Pharm Sci 85: 1017-1025 (1996)). The solubility of human growth hormone was improved by CDs present at about 2-6%, with alpha and gamma cyclodextrins found to be several-fold less effective than beta cyclodextrins. (Otzen, D. E. et al., Protein Sci. 11:1779-1787 (2002)).

Whilst the primary sequence of an antibody define its pI and it's intrinsically responsible of its tendency to precipitate upon administration (e.g. pH shift), the formulation composition will additionally affect this behavior and also influence other properties, including viscosity and osmolality. Altered interactions between the excipients and the active ingredients in the formulation may affect its long term stability. This is particularly relevant for antibody formulations developed for subcutaneous administration, where a high protein concentration meets a lower administration volume and protein aggregation and precipitation become even more apparent and potentially responsible for injection side effects.

Given the above, there remains a need in the art to provide further improved liquid pharmaceutical formulations of antibodies with reduced protein aggregation and precipitation, especially for formulations for subcutaneous route of administration.

SUMMARY OF THE INVENTION

The present invention addresses the above-identified need by providing a novel liquid formulation comprising an antibody or an antigen-binding fragment as active ingredient. A synergistic stabilizing effect has now been surprisingly observed between stabilizers with respect to the appearance of aggregates (precipitates) in a liquid pharmaceutical formulation.

Therefore, in a first aspect, the invention provides for a liquid pharmaceutical formulation comprising an antibody or an antigen-binding fragment thereof, as an active ingredient, cyclodextrin and methionine.

In a first embodiment of this aspect the liquid pharmaceutical formulation comprises methionine at a concentration of from 7.5 mM to 200 mM.

In a second embodiment the liquid pharmaceutical formulation according to the first aspect and embodiment comprises cyclodextrin at a concentration of from 7.5 mM to 250 mM.

In a third embodiment the liquid pharmaceutical formulation according to the first aspect and its embodiments comprises an antibody or an antigen-binding fragment thereof at a concentration of from 1 to 200 mg/ml, preferably from 90 to 180 mg/ml. In a fourth embodiment the liquid pharmaceutical formulation according to the first aspect and its embodiments comprises an antibody or an antigen-binding fragment thereof which specifically binds to human sclerostin and/or is a human or humanized antibody.

In a fifth embodiment the liquid pharmaceutical formulation according to the first aspect and its embodiments comprises:
1. an antibody or antigen-binding fragment thereof which
   a. comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6; or
   b. has a light variable region having the sequence as defined in SEQ ID NO: 7 and a heavy variable region having the sequence as defined in SEQ ID NO: 8; or
2. an antibody which has
   a. a light chain having the sequence as defined in SEQ ID NO: 9 and a heavy chain having the sequence as defined in SEQ ID NO: 10; or
   b. a light chain having the sequence as defined in SEQ ID NO: 11 and a heavy chain having the sequence as defined in SEQ ID NO: 12.

In a sixth embodiment the liquid pharmaceutical formulation according to the first aspect and its embodiments comprises an antibody which is romosozumab.

In a seventh embodiment, liquid formulation according to the first aspect and its embodiments has pH of from 4.0 to 7.5.

In an eight embodiment the liquid formulation according to the first aspect and its embodiments comprises a cyclodextrin selected from alpha-cyclodextrin, beta-cyclodextrin, dimethyl-beta-cyclodextrin, trimethyl-beta-cyclodextrin, randomly methylated beta-cyclodextrin, hydroxyethyl-beta-cyclodextrin, hydroxypropyl-beta-cyclodextrin (i.e. 2 hydroxypropyl-beta-cyclodextrin, 3-hydroxypropyl-beta-cyclodextrin or 2,3-dihydroxypropyl-beta-cyclodextrin), hydroxyisobutyl-beta-cyclodextrin sulfobutylether beta-cyclodextrin, glucosyl-beta-cyclodextrin, maltosyl-beta-cyclodextrin, gamma-cyclodextrin, hydroxypropyl-gamma-cyclodextrin (i.e. 2 hydroxypropyl-gamma-cyclodextrin, 3-hydroxypropyl-gamma-cyclodextrin or 2,3-dihydroxypropyl-gamma-cyclodextrin), cyclodextrin-containing polymers or combinations thereof. Preferably, the cyclodextrin is selected from hydroxypropyl-gamma-cyclodextrin.

In an ninth embodiment the liquid formulation according to the first aspect and its embodiments comprises from 1 mg/ml to 200 mg/ml of antibody, from 10 mM to 55 mM sodium acetate, from 0 to 14 mM calcium acetate, from 0 to 6% sucrose, from 0 to 0.006% polysorbate 20, from 55 mM to 80 mM hydroxypropyl-gamma-cyclodextrin, from 55 mM to 160 mM methionine at pH 5.2; preferably form 90 mg/ml to 180 mg/ml, more preferably from 120 mg/ml to 180 mg/ml of romosozumab.

In a second aspect the present invention provides for the liquid formulation according to the first aspect and its embodiments for use in the treatment of a bone disorder associated with at least one of low bone formation, low bone mineral density, low bone mineral content, low bone mass, low bone quality and low bone strength. Alternatively, the present invention provides for the use of the liquid formulation according to the first aspect and its embodiments in the manufacture of a medicament for the treatment of a bone disorder associated with at least one of low bone formation, low bone mineral density, low bone mineral content, low bone mass, low bone quality and low bone strength.

Furthermore, in a third aspect the present invention provides for a method for treating a bone disorder associated with at least one of low bone formation, low bone mineral density, low bone mineral content, low bone mass, low bone quality and low bone strength in a mammalian subject comprising administering a therapeutically effective amount of the formulation according to the first aspect and its embodiments.

Preferably, in embodiments of the second and third aspects of the invention, the bone disorder is osteoporosis.

In a fourth aspect the invention provides for a method for reducing precipitation of an antibody or an antigen-binding fragment thereof in a liquid pharmaceutical formulation, the method comprising providing a liquid formulation and adding to the formulation methionine and cyclodextrin, preferably hydroxylpropyl-gamma-cyclodextrin.

Finally, in a fifth aspect, the present invention provides for a method of reducing inflammation at injection site in a mammalian subject comprising administering a therapeutically effective amount of the formulation according to the first aspect and its embodiments.

BRIEF DESCRIPTION OF THE DRAWINGS

FIG. 1 shows the sequence of the light chain of romosozumab (SEQ ID NO: 11). The amino acid sequence is presented using three-letter symbols with the corresponding one-letter symbol beneath each amino acid. Intrachain disulfide bonds are indicated by lines between linked cysteines. Cysteines forming interchain bonds are indicated in boxes.

FIG. 2 shows the sequence of the heavy chain of romosozumab (SEQ ID NO: 12). The amino acid sequence is presented using three-letter symbols with the corresponding one-letter symbol beneath each amino acid. Intrachain disulfide bonds are indicated by lines between linked cysteines. Cysteines forming interchain bonds are indicated in boxes.

DETAILED DESCRIPTION OF THE INVENTION

The liquid pharmaceutical formulation according to the invention comprises an antibody or an antigen-binding fragment thereof as active ingredient, and the combination of two stabilizers, methionine and cyclodextrin.

The synergistic combination of methionine and cyclodextrin provides the additional advantages of reducing the rate of precipitation of the antibody or the antigen-binding fragment thereof in the form of aggregates over time thus potentially reducing the occurrence of injection side reactions. Therefore, the present invention also provides for a method for reducing precipitation of an antibody or antigen-binding fragment thereof in a liquid pharmaceutical formulation, the method comprising providing a liquid formulation and adding to the formulation methionine and cyclodextrin.

The concentration of cyclodextrin in the liquid pharmaceutical formulation may be from 7.5 mM to 250 mM, or from 16 mM to 250 mM, or from 32 mM to 200 mM, or from 63 mM to 160 mM or preferably from 55 mM to 80 mM.

The concentration of methionine in the liquid pharmaceutical formulation may be from 7.5 mM to 200 mM or from 15 mM to 200 mM or from 30 mM to 200 mM or from 55 mM to 160 mM or preferably from 55 mM to 125 mM.

In one embodiment, the liquid pharmaceutical formulation according to the invention comprises an antibody or antigen binding fragment thereof as active ingredient and a ratio of from 1:1 to 1:3, preferably a ratio of 1:2 of cyclodextrin to methionine.

In one preferred embodiment, the liquid pharmaceutical formulation according to the invention comprises an antibody or an antigen-binding fragment thereof as active ingredient, from 55 mM to 160 mM of methionine and from 55 mM to 100 mM of cyclodextrin.

In particular, the cyclodextrin may be selected from alpha-cyclodextrin, beta-cyclodextrin, dimethyl-beta-cyclodextrin, trimethyl-beta-cyclodextrin, randomly methylated beta-cyclodextrin, hydroxyethyl-beta-cyclodextrin, hydroxypropyl-beta-cyclodextrin (i.e. 2 hydroxypropyl-beta-cyclodextrin, 3-hydroxypropyl-beta-cyclodextrin or 2,3-dihydroxypropyl-beta-cyclodextrin), hydroxyisobutyl-beta-cyclodextrin sulfobutylether beta-cyclodextrin, glucosyl-beta-cyclodextrin, maltosyl-beta-cyclodextrin, gamma-cyclodextrin, hydroxypropyl-gamma-cyclodextrin (i.e. 2 hydroxypropyl-gamma-cyclodextrin, 3-hydroxypropyl-gamma-cyclodextrin or 2,3-dihydroxypropyl-gamma-cyclodextrin), cyclodextrin-containing polymers or combinations thereof.

The most common natural cyclodextrins are alpha-cyclodextrin, beta-cyclodextrin and gamma-cyclodextrin, all of which are hydrophilic. Substitutions of the hydroxyl groups further enhance the cyclodextrin solubility (Loftsson T. et al, Expert Opin. Drug Deliv. 2, 335-351 (2005); Davis M. E. & Brewster M. E., Nature Reviews—Drug discovery 3, 1023-1035 (2004)).

Chemically modified (i.e. substituted at the hydroxyl groups) cyclodextrins of interest are mono, di or trimethyl-beta-cyclodextrin, randomly methylated beta-cyclodextrin, hydroxyethyl-beta-cyclodextrin, hydroxypropyl-beta-cyclodextrin (i.e. 2 hydroxypropyl-beta-cyclodextrin, 3-hydroxypropyl-beta-cyclodextrin or 2,3-dihydroxypropyl-beta-cyclodextrin), hydroxyisobutyl-beta-cyclodextrin sulfobutylether beta-cyclodextrin, glucosyl-beta-cyclodextrin, maltosyl-beta-cyclodextrin, hydroxypropyl-gamma-cyclodextrin (i.e. 2 hydroxypropyl-gamma-cyclodextrin, 3-hydroxypropyl-gamma-cyclodextrin or 2,3-dihydroxypropyl-gamma-cyclodextrin) or combination thereof.

Hence, the liquid pharmaceutical formulation according to the invention comprises an antibody or an antigen-binding fragment thereof as active ingredient, and the combination of methionine and a chemically modified cyclodextrin, preferably selected from mono, di or trimethyl-beta-cyclodextrin, randomly methylated beta-cyclodextrin, hydroxyethyl-beta-cyclodextrin, hydroxypropyl-beta-cyclodextrin (i.e. 2 hydroxypropyl-beta-cyclodextrin, 3-hydroxypropyl-beta-cyclodextrin or 2,3-dihydroxypropyl-beta-cyclodextrin), hydroxyisobutyl-beta-cyclodextrin sulfobutylether beta-cyclodextrin, glucosyl-beta-cyclodextrin, maltosyl-beta-cyclodextrin, hydroxypropyl-gamma-cyclodextrin (i.e. 2 hydroxypropyl-gamma-cyclodextrin, 3-hydroxypropyl-gamma-cyclodextrin or 2,3-dihydroxypropyl-gamma-cyclodextrin) or combination thereof.

The concentration of the chemically modified cyclodextrin in the liquid pharmaceutical formulation may be from 7.5 mM to 250 mM, or from 16 mM to 250 mM, or from 32 mM to 200 mM, or from 63 mM to 160 mM or preferably from 55 mM to 80 mM.

In one embodiment, the liquid pharmaceutical formulation according to the invention comprises an antibody or antigen binding fragment thereof as active ingredient and a ratio of from 1:1 to 1:3, preferably a ratio of 1:2 of chemically modified cyclodextrin to methionine.

In one preferred embodiment, the liquid pharmaceutical formulation according to the invention comprises an antibody or an antigen-binding fragment thereof as active ingredient, from 55 mM to 160 mM of methionine and from 55 mM to 100 mM of a chemically modified cyclodextrin.

The preferred cyclodextrin according to the present invention is hydroxypropyl-gamma-cyclodextrin such as 2 hydroxypropyl-gamma-cyclodextrin, 3-hydroxypropyl-gamma-cyclodextrin, 2,3-dihydroxypropyl-gamma-cyclodextrin or combinations thereof.

Hence, in one preferred embodiment, the liquid pharmaceutical formulation according to the invention comprises an antibody or an antigen-binding fragment thereof as active ingredient, and the combination of methionine and hydroxypropyl-beta-cyclodextrin (i.e. 2 hydroxypropyl-beta-cyclodextrin, 3-hydroxypropyl-beta-cyclodextrin, 2,3-dihydroxypropyl-beta-cyclodextrin or combinations thereof).

The concentration of hydroxypropyl-gamma-cyclodextrin in the liquid pharmaceutical formulation may be from 7.5 mM to 250 mM, or from 16 mM to 250 mM, or from 32 mM to 200 mM, or from 63 mM to 160 mM or preferably from 55 mM to 80 mM.

In another embodiment, the liquid pharmaceutical formulation according to the invention comprises an antibody or antigen binding fragment thereof as active ingredient and a ratio of from 1:1 to 1:3, preferably a ratio of 1:2 of hydroxypropyl-gamma-cyclodextrin to methionine.

In another embodiment, the liquid pharmaceutical formulation according to the invention comprises an antibody or an antigen-binding fragment thereof as active ingredient, from 55 mM to 160 mM of methionine and from 55 mM to 100 mM of hydroxypropyl-gamma-cyclodextrin.

The concentration of antibody or antigen-binding fragment thereof in the liquid formulation according to the present invention may be from 1 to 200 mg/ml, or from to 200 mg/ml, or from to 200 mg/ml or preferably from 90 to 180 mg/ml. In another embodiment, the liquid pharmaceutical formulation according to the invention comprises from 90 mg/ml to 180 mg/ml of an antibody as active ingredient, from 55 mM to 160 mM of methionine and from 55 mM to 100 mM of cyclodextrin.

In particular, the cyclodextrin may be selected from beta-cyclodextrin, dimethyl-beta-cyclodextrin, trimethyl-beta-cyclodextrin, randomly methylated beta-cyclodextrin, hydroxyethyl-beta-cyclodextrin, hydroxypropyl-beta-cyclodextrin (i.e. 2 hydroxypropyl-beta-cyclodextrin, 3-hydroxypropyl-beta-cyclodextrin or 2,3-dihydroxypropyl-beta-cyclodextrin), hydroxyisobutyl-beta-cyclodextrin sulfobutylether beta-cyclodextrin, glucosyl-beta-cyclodextrin, maltosyl-beta-cyclodextrin, gamma-cyclodextrin, hydroxypropyl-gamma-cyclodextrin (i.e. 2 hydroxypropyl-gamma-cyclodextrin, 3-hydroxypropyl-gamma-cyclodextrin or 2,3-dihydroxypropyl-gamma-cyclodextrin), cyclodextrin-containing polymers or combinations thereof.

In another embodiment, the liquid pharmaceutical formulation according to the invention comprises from 90 mg/ml to 180 mg/ml of an antibody as active ingredient, from 55 mM to 160 mM of methionine and from 55 mM to 100 mM of a chemically modified cyclodextrin, preferably selected from mono, di or trimethyl-beta-cyclodextrin, randomly methylated beta-cyclodextrin, hydroxyethyl-beta-cyclodextrin, hydroxypropyl-beta-cyclodextrin (i.e. 2 hydroxypropyl-beta-cyclodextrin, 3-hydroxypropyl-beta-cyclodextrin or 2,3-dihydroxypropyl-beta-cyclodextrin), hydroxyisobutyl-beta-cyclodextrin sulfobutylether beta-cyclodextrin, glucosyl-beta-cyclodextrin, maltosyl-beta-cyclodextrin, hydroxypropyl-gamma-cyclodextrin (i.e. 2 hydroxypropyl-gamma-cyclodextrin, 3-hydroxypropyl-gamma-cyclodextrin or 2,3-dihydroxypropyl-gamma-cyclodextrin) or combinations thereof.

In one preferred embodiment, the liquid pharmaceutical formulation according to the invention comprises from 90 mg/ml to 180 mg/ml of an antibody as active ingredient, from 55 mM to 160 mM of methionine and from 55 mM to 100 mM of hydroxypropyl-gamma-cyclodextrin such as 2 hydroxypropyl-gamma-cyclodextrin, 3-hydroxypropyl-gamma-cyclodextrin, 2,3-dihydroxypropyl-gamma-cyclodextrin or combinations thereof.

The active ingredient comprised in the liquid pharmaceutical formulation according to the invention is preferably an antibody. Preferably the antibody has an isoelectric point (pI) lower than the physiological pH (~7.0) but higher than the formulation pH. In one embodiment the liquid formulation according to the present invention and its embodiments comprises from 1 to 200 mg/ml of an antibody, wherein the antibody has a pI of from 5.0 to 6.9, preferably from 5.3 to 6.9.

Preferably the antibody comprised in the liquid pharmaceutical formulation according to the invention specifically binds to human sclerostin.

The term "specifically binds to human sclerostin", "specifically binding to human sclerostin", and equivalents as used herein when referring to an antibody means the antibody will bind to human sclerostin with sufficient affinity and specificity to achieve a biologically meaningful effect. The antibody selected will normally have a binding affinity for human sclerostin, for example, the antibody may bind human sclerostin with a Kd value of between 100 nM and 1 pM. Antibody affinities may be determined by a surface plasmon resonance bases assay, such as the BIAcore assay; enzyme-linked immunoabsorbent assay (ELISA); and competition assays (e.g. RIA's), for example. Within the meaning of the present invention an antibody specifically binding to human sclerostin may also bind to another molecule, e.g. mouse sclerostin or such as by way of a non-limiting example in the case of a bispecific antibody.

Sclerostin, a protein encoded by the SOST gene, is a glycoprotein secreted by osteocytes and is a potent inhibitor of osteoblastogenesis. Loss-of-function mutations in SOST are associated with an autosomal-recessive disorder, sclerosteosis, which causes progressive bone overgrowth. A deletion downstream of the SOST gene, which results in reduced sclerostin expression, is associated with a milder form of the disease called van Buchem disease. Furthermore, SOST-null mice have a high-bone-mass phenotype.

The antibody or antigen-binding fragment thereof binding specifically to human sclerostin, preferably also neutralizes human sclerostin.

The term "neutralizes" as used herein refers to an antibody that inhibits or substantially reduces the biological effect of the molecule to which it specifically binds. Therefore, the expression "the antibody neutralizes human sclerostin" refers to an antibody that specifically binds to human sclerostin and inhibits or substantially reduces the biological effect thereof.

The term "antibody" or "antibodies" as used herein refers to monoclonal or polyclonal antibodies. The term "antibody" or "antibodies" as used herein includes but is not limited to recombinant antibodies that are generated by recombinant technologies as known in the art.

Preferably, the antibody comprised in the liquid formulation according to the invention is a monoclonal antibody which specifically binds human sclerostin.

"Antibody" or "antibodies" include antibodies' of any species, in particular of mammalian species, having two essentially complete heavy and two essentially complete light chains, human antibodies of any isotype, including $IgA_1$, $IgA_2$, IgD, $IgG_1$, $IgG_{2a}$, $IgG_{2b}$, $IgG_3$, $IgG_4$ IgE and IgM and modified variants thereof, non-human primate antibodies, e.g. from chimpanzee, baboon, rhesus or cynomolgus monkey, rodent antibodies, e.g. from mouse, rat or rabbit; goat or horse antibodies, and camelid antibodies (e.g. from camels or llamas such as Nanobodies™) and derivatives thereof, or of bird species such as chicken antibodies or of fish species such as shark antibodies. The term "antibody" or "antibodies" also refers to "chimeric" antibodies in which a first portion of at least one heavy and/or light chain antibody sequence is from a first species and a second portion of the heavy and/or light chain antibody sequence is from a second species. Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences. "Humanized" antibodies are chimeric antibodies that contain a sequence derived from non-human antibodies. For the most part, humanized antibodies are human antibodies (recipient antibody) in which residues from a hypervariable region of the recipient are replaced by residues from a hypervariable region [or complementarity determining region (CDR)] of a non-human species (donor antibody) such as mouse, rat, rabbit, chicken or non-human primate, having the desired specificity, affinity, and activity. In most instances residues of the human (recipient) antibody outside of the CDR; i.e. in the framework region (FR), are additionally replaced by corresponding non-human residues. Furthermore, humanized antibodies may comprise residues that are not found in the recipient antibody or in the donor antibody. These modifications are made to further refine antibody performance. Humanization reduces the immunogenicity of non-human antibodies in humans, thus facilitating the application of antibodies to the treatment of human diseases. Humanized antibodies and several different technologies to generate them are well known in the art. The term "antibody" or "antibodies" also refers to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies with specificity against a particular antigen upon immunization of the transgenic animal carrying the human germ-line immunoglobulin genes with said antigen. Technologies for producing such transgenic animals and technologies for isolating and producing the human antibodies from such transgenic animals are known in the art. Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development are essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody. The term "antibody" or "antibodies" as used herein, also refers to an aglycosylated antibody.

The term "antigen-binding fragment thereof" or grammatical variations thereof as used herein refers to an antibody fragment. A fragment of an antibody comprises at least one heavy or light chain immunoglobulin domain as known in the art and binds to one or more antigen(s). Examples of antibody fragments according to the invention include Fab, Fab', F(ab')$_2$, and Fv and scFv fragments; as well as diabodies, triabodies, tetrabodies, minibodies, domain antibodies (dAbs), such as sdAbs, VHH and VNAR fragments, single-chain antibodies, bispecific, trispecific, tetraspecific or multispecific antibodies formed from antibody fragments or antibodies, including but not limited to Fab-Fv or Fab-Fv-Fv constructs. Antibody fragments as defined above are known in the art.

The antibody or antigen-binding fragment thereof comprised as active ingredient in the liquid pharmaceutical formulation according to the invention may be human or humanized antibody, preferably a humanized monoclonal antibody which specifically binds human sclerostin.

1) More preferably the liquid pharmaceutical formulation according to the invention comprises: an antibody or antigen-binding fragment thereof which a. comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6; or b. has a light variable region having the sequence as defined in SEQ ID NO: 7 and a heavy variable region having the sequence as defined in SEQ ID NO: 8; or 2) an antibody which has a. a light chain having the sequence as defined in SEQ ID NO: 9 and a heavy chain having the sequence as defined in SEQ ID NO: 10; or b. a light chain having the sequence as defined in SEQ ID NO: 11 and a heavy chain having the sequence as defined in SEQ ID NO: 12.

Throughout this specification, complementarity determining regions ("CDR") are defined according to the Kabat definition. The Kabat definition is a standard for numbering the residues in an antibody and it is typically used to identify CDR regions (Kabat et al., (1991), 5th edition, NIH publication No. 91-3242).

Figure 2:
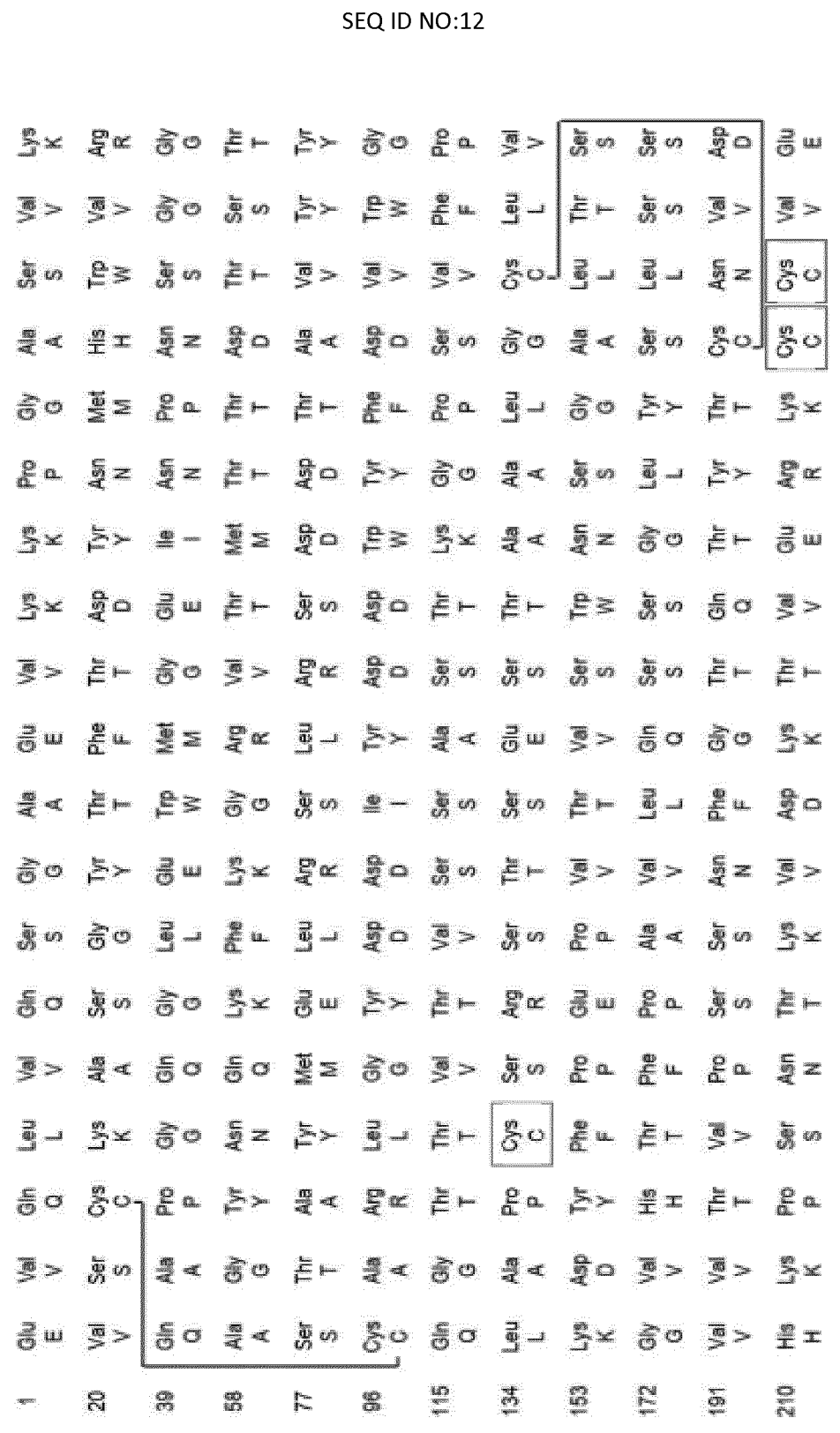

The sequences are shown in Table 1 below and in FIGS. 1 and 2.

TABLE 1

| Region and SEQ ID identifier | Amino acid sequence |
|---|---|
| CDR-H1 SEQ ID NO: 1 | DYNMH |
| CDR-H2 SEQ ID NO: 2 | EINPNSGGAGYNQKFKG |
| CDR-H3 SEQ ID NO: 3 | LGYDDIYDDWYFDV |
| CDR-L1 SEQ ID NO: 4 | RASQDISNYLN |
| CDR-L2 SEQ ID NO: 5 | YTSRLLS |
| CDR-L3 SEQ ID NO: 6 | QQGDTLPYT |
| Light variable region SEQ ID NO: 7 | DIQMTQSPSSLSASVGDRVTITCRASQDISNYLN WYQQKPGKAPKLLIYYTSRLLSGVPSRFSGSGSG TDFTLTISSLQPEDFATYYCQQGDTLPYTFGGGT KVEIK |
| Heavy variable region SEQ ID NO: 8 | EVQLVQSGAEVKKPGASVKVSCKASGYTFTDYNM HWVRQAPGQGLEWMGEINPNSGGAGYNQKFKGRV TMTTDTSTSTAYMELRSLRSDDTAVYYCARLGYD DIYDDWYFDVWGQGTTVTVSS |
| Light chain SEQ ID NO: 9 | DIQMTQSPSSLSASVGDRVTITCRASQDISNYLN WYQQKPGKAPKLLIYYTSRLLSGVPSRFSGSGSG TDFTLTISSLQPEDFATYYCQQGDTLPYTFGGGT KVEIKRTVAAPSVFIFPPSDEQLKSGTASVVCLL ANNFYPREAKVQWKVDNLQSGNSQESVTEQDSKD STYSLSSTLTLSKADYEKHKVYACEVTHQGLSSP VTKSFNRGEC |
| Heavy chain SEQ ID NO: 10 | EVQLVQSGAEVKKPGASVKVSCKASGYTFTDYNM HWVRQAPGQGLEWMGEINPNSGGAGYNQKPKGRV TMTTDTSTSTAYMELRSLRSDDTAVYYCARLGYD DIYDDWYFDVWGQGTTVTYSSASTKGPSVFPLAP CSRSTSESTAALGCLVKDYFPEPVTVSWNSGALT SGVHTFPAVLQSSGLYSLSSVVTVPSSNFGTQTY TCNVDHKPSNTKVDKTVERKCCVECPPCPAPPVA GPSVFLFPPKPKDTLMISRTPEVTCVVVDVSHED PEVQFNWYVDGVEVHNAKTKPREEQFNSTFRVVS VLTVVHQDWLNGKEYKCKVSNKGLPAPIEKTISK TKGQPREPQVYTLPPSREEMTKNQVSLTCLVKGF YPSDIAVEWESNGQPENNYKTTPPMLDSDGSFFL YSKLTVDKSRWQQGNVFSCSVMHEALHNHYTQKS LSLSPGK |

Even more preferably, the antibody comprised as active ingredient in the liquid pharmaceutical formulation according to the invention is romosozumab, an anti-human sclerostin antibody as described in WO2006119107 and WO2011143307 (incorporated herein by reference).

In particular, the present invention also provides for a liquid pharmaceutical formulation comprising romosozumab and a cyclodextrin, preferably selected from alpha-cyclodextrin, beta-cyclodextrin, dimethyl-beta-cyclodextrin, trimethyl-beta-cyclodextrin, randomly methylated beta-cyclodextrin, hydroxyethyl-beta-cyclodextrin, hydroxypropyl-beta-cyclodextrin (i.e. 2 hydroxypropyl-beta-cyclodextrin, 3-hydroxypropyl-beta-cyclodextrin or 2,3-dihydroxypropyl-beta-cyclodextrin), hydroxyisobutyl-beta-cyclodextrin sulfobutylether beta-cyclodextrin, glucosyl-beta-cyclodextrin, maltosyl-beta-cyclodextrin, gamma-cyclodextrin, hydroxypropyl-gamma-cyclodextrin (i.e. 2 hydroxypropyl-gamma-cyclodextrin, 3-hydroxypropyl-gamma-cyclodextrin or 2,3-dihydroxypropyl-gamma-cyclodextrin), cyclodextrin-containing polymers or combinations thereof, more preferably the liquid pharmaceutical formulation comprising romosozumab and hydroxypropyl-gamma-cyclodextrin.

The liquid pharmaceutical formulation according to any of the embodiments of the invention may contain a buffering agent to maintain a constant pH during storage and administration. There are many buffering agents used in the field of liquid pharmaceutical formulations, such as, but not limited to, citrate, phosphate, lactate, histidine, glutamate, maleate, tartrate, or succinate. A preferred buffer species is typically selected amongst those having a pKa that is close (+/−1 pH unit) to the preferred pH for optimal protein stability in order to maintain high buffering capacity, and is associated with the maximal demonstrated stability observed for a particular protein when placed in a series of varied buffer species. The adequate pH ranges of a formulation are generally chosen from those associated with the maximal demonstrated stability observed for a particular protein when placed in a series of varied pH formulations.

In a particular embodiment of the invention, the liquid pharmaceutical formulation according to any of the embodiments of the invention comprises sodium acetate, preferably at a concentration of 10 mM to 100 mM, 10 mM to 80 mM, 10 mM to 60 mM, 25 mM to 60 mM, preferably 40 mM to 60 mM, or 50 mM. The liquid pharmaceutical formulation according to the invention may also comprise calcium acetate, preferably at a concentration of 0.5 mM to 50 mM, 5 mM to 40 mM, 10 mM to 30 mM or 14 mM. More preferably, the liquid pharmaceutical formulation according to the invention comprises 50 mM sodium acetate and 14 mM calcium acetate.

In a further embodiment, the liquid pharmaceutical formulation according to any of the embodiments of the invention may have a pH of 4 to 7.5, preferably 4 to 6, preferably 4.5 to 5.5, or 5.2.

In a further embodiment the liquid pharmaceutical formulation according to any of the embodiments of the invention additionally comprises a surfactant. The skilled artisan is aware of the choice of surfactants available for use in the liquid formulation according to any of the embodiments of the invention such as but not limited to polysorbate 80, polysorbate 20, lecithin, poloxamer (e.g. poloxamer 188), sodium dodecyl sulfate (SDS), sodium laurel sulfate, sodium octyl glycoside, lauryl-, myristyl-, linoleyl-, or stearyl-sulfobetaine, lauryl-, myristyl-, linoleyl- or stearyl-sarcosine, linoleyl-, myristyl-, or cetyl-betaine, lauroamidopropyl-, cocamidopropyl-, linoleamidopropyl-, myristamidopropyl-, palmidopropyl-, or isostearamidopropyl-betaine, myristamidopropyl-, palmidopropyl-, or isostearamidopropyl-dimethylamine, sodium methyl cocoyl-, or disodium methyl oleyl-taurate, polyethyl glycol, polypropyl glycol, and copolymers of ethylene and propylene glycol. In a further embodiment of the invention, the liquid pharmaceutical formulation may comprise polysorbate 20.

The liquid formulation of the invention may comprise from 0.001% to 10% Polysorbate 20, from 0.001% to 5% Polysorbate 20, from 0.001 to 1% Polysorbate 20, from 0.001 to 0.006% Polysorbate 20, or 0.006% Polysorbate 20.

The liquid formulation according to the embodiments of the invention may further comprise additional excipients commonly used in the preparation of liquid pharmaceutical formulations including but not limited to sugars (e.g. sucrose or treahalose), poly-ethylene glycols (e.g. PEG100, PEG300, PEG600, PEG1500, PEG2000, PEG3000, PEG3350, PEG4000, PEG6000, PEG8000 or PEG20000), polyols (e.g. mannitol, sorbitol or lactitol), other amino acids than methionine, polyvinylpyrrolidone, trimethylamine N-oxide, trimethylglycine or combinations thereof.

In particular, the liquid formulation according to the embodiments of the invention may further comprise sucrose, from 0 to 6% sucrose, more preferably 6% sucrose.

In an another embodiment the liquid pharmaceutical formulation according to any of the embodiments of the invention comprises from 1 mg/ml to 200 mg/ml of antibody, from 10 mM to 55 mM sodium acetate, from 0 to 14 mM calcium acetate, from 0 to 6% sucrose, from 0 to 0.006% polysorbate 20, from 55 mM to 80 mM of a chemically modified cyclodextrin, from 55 mM to 160 mM methionine at pH 5.2; more preferably form 90 mg/ml to 180 mg/ml and even more preferably from 120 mg/ml to 180 mg/ml of antibody, wherein the chemically modified cyclodextrin is preferably selected from mono, di or trimethyl-beta-cyclodextrin, randomly methylated beta-cyclodextrin, hydroxyethyl-beta-cyclodextrin, hydroxypropyl-beta-cyclodextrin (i.e. 2 hydroxypropyl-beta-cyclodextrin, 3-hydroxypropyl-beta-cyclodextrin or 2,3-dihydroxypropyl-beta-cyclodextrin), hydroxyisobutyl-beta-cyclodextrin sulfobutylether beta-cyclodextrin, glucosyl-beta-cyclodextrin, maltosyl-beta-cyclodextrin, hydroxypropyl-gamma-cyclodextrin (i.e. 2 hydroxypropyl-gamma-cyclodextrin, 3-hydroxypropyl-gamma-cyclodextrin or 2,3-dihydroxypropyl-gamma-cyclodextrin) or combinations thereof.

In a further embodiment the liquid pharmaceutical formulation according to any of the embodiments of the invention comprises from 1 mg/ml to 200 mg/ml of antibody, from 10 mM to 55 mM sodium acetate, from 0 to 14 mM calcium acetate, from 0 to 6% sucrose, from 0 to 0.006% polysorbate 20, from 55 mM to 80 mM hydroxypropyl-gamma-cyclodextrin, from 55 mM to 160 mM methionine at pH 5.2; more preferably form 90 mg/ml to 180 mg/ml and even more preferably from 120 mg/ml to 180 mg/ml of antibody.

In a preferred embodiment, the liquid pharmaceutical formulation according to the invention comprises at least 90 mg/ml antibody, 55 mM hydroxypropyl-gamma-cyclodextrin, 125 mM methionine 55 mM sodium acetate buffer at pH 5, 14 mM calcium acetate, 6% sucrose and 0.006% polysorbate 20, wherein the antibody is an anti-human sclerostin antibody. Even more preferably the liquid pharmaceutical formulation according to the invention comprises at least 90 mg/ml antibody, 55 mM hydroxypropyl-gamma-cyclodextrin, 125 mM methionine 55 mM sodium acetate buffer at pH 5, 14 mM calcium acetate, 6% sucrose and 0.006% polysorbate 20, wherein the antibody is an anti-human sclerostin antibody and the formulation is for subcutaneous administration.

In another embodiment the liquid pharmaceutical formulation according to any of the embodiments of the invention exhibits an osmolality of 800 mOsm/l or less and/or a viscosity of 80 cP or less.

In an embodiment the liquid formulation is not a hydrogel. In an embodiment the liquid formulation comprises at least 2%, at least 5%, at least 10%, at least 25%, between 2% and 90%, between 2% and 75%, or between 2% and 50% water.

The liquid pharmaceutical formulation according to any of the embodiments of the invention may be used in the treatment of a bone disorder associated with at least one of low bone formation, low bone mineral density, low bone mineral content, low bone mass, low bone quality and low bone strength. In addition, the invention provides for a method of treating a bone disorder associated with at least one of low bone formation, low bone mineral density, low bone mineral content, low bone mass, low bone quality and low bone strengthin a mammalian subject comprising administering a therapeutically effective amount of the liquid pharmaceutical formulation according to any of the embodiments of the invention. Furthermore, the invention provides for the use of the liquid formulation according to any one of the embodiments of the invention for the manufacture of a medicament for the treatment of a bone disorder associated with at least one of low bone formation, low bone mineral density, low bone mineral content, low bone mass, low bone quality and low bone strength.

The mammalian subject may be selected from the group of rodents, cats, dogs, horses, bovine, ovine, non-human primates and human subjects. Preferably, the mammalian subject is a human subject.

The invention is typically used to treat or help prevent a bone disorder associated with at least one of low bone formation, low bone mineral density, low bone mineral content, low bone mass, low bone quality and low bone strength. The bone disorder is characterized by an altered function of sclerostin or by an increased/decreased expression of sclerostin protein in relevant tissue (e.g. bone, cartilage). The invention may be, for example, employed to increase at least one of bone formation, bone mineral density, bone mineral content, bone mass, bone quality and bone strength.

The bone disorder may be associated with abnormal osteoblast or osteoclast activity, with decreased bone density, increased bone resorption and/or bone-related disorders, i.e. osteoporosis. In particular, the bone disorder may be selected from the group of achondroplasia, cleidocranial dysostosis, enchondromatosis, fibrous dysplasia, Gaucher's Disease, hypophosphatemia rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthes' Disease, adolescent idiopathic scoliosis, infantile onset multi-system inflammatory disease, Winchester Syndrome, Menkes Disease, Wilson's Disease, ischemic bone disease (such as Legg-Calve-Perthes disease, regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone gap defect, alveolar bone loss, bone loss associated with joint replacement, HIV associated bone loss, bone loss associated with loss of growth hormone, bone loss associated with cystic fibrosis, chemotherapy associated bone loss, tumor induced bone loss, cancer-related bone loss, hormone ablative bone loss, multiple myeloma, drug-induced bone loss, anorexia nervosa, disease associated facial bone loss, disease associated cranial bone loss, disease associated bone loss of the jaw, disease associated bone loss of the skull, bone loss associated with aging, facial bone loss associated with aging, cranial bone loss associated with aging, jaw bone loss associated with aging, skull bone loss associated with aging and bone loss associated with space travel and combinations thereof.

Bone loss, decreased bone mineral density, decreased bone volume, and/or decreased bone mineral content associated with these disorders may be treated in the context of the invention. In one instance, the subject to be treated may be pregnant. For instance, the invention may be employed to help in pregnancy-related bone loss. The invention may be used to slow, or reverse, bone loss in general.

In one preferred embodiment, the bone disorder to be treated is osteoporosis or osteopenia. In one instance, the mammalian subject to be treated is a postmenopausal woman, for instance, one with osteoporosis, particularly such a subject who is at increased, or high risk, for fracture, or has failed or is intolerant to other available osteoporosis therapy. In further instances, the invention may be employed in improving the outcome in a mammal undergoing one or more of an orthopedic procedure, dental procedure, implant surgery, joint replacement, bone grafting, bone cosmetic surgery and bone repair such as fracture healing, nonunion healing, delayed union healing and facial reconstruction.

In another preferred embodiment, the subject has, or is thought at risk of, a bone fracture. For instance, it may be that the subject has a bone mineral density that identifies them at risk of bone fracture. It may be that the subject has recently been diagnosed with a bone disorder as a result of a bone fracture. In some instances, it may be that the subject has a fracture of the wrist, arm, leg, hip or vertebrae and in some cases it may be that the fracture has resulted in the diagnosis of the bone disorder.

Preferably, the bone disorder is selected from osteoporosis, bone gap defect, alveolar bone loss, inhibited bone resorption or combinations thereof.

The present invention also provides for a method for reducing inflammation at injection site in a mammalian subject comprising administering a therapeutically effective amount of the liquid pharmaceutical formulation according to any of the embodiments of the invention.

The liquid pharmaceutical formulations according to the invention are administered in a therapeutically effective amount. The term "therapeutically effective amount" as used herein refers to an amount of a therapeutic agent (i.e. active ingredient) needed to treat, ameliorate or prevent a targeted disease, disorder or condition, or to exhibit a detectable therapeutic, pharmacological or preventative effect. For any antibody or antigen-binding fragments thereof, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount of antibody will be from 0.01 mg/kg to 500 mg/kg, for example 0.1 mg/kg to 200 mg/kg, such as 100 mg/kg.

The liquid pharmaceutical formulation may be conveniently presented in unit dose forms containing a predetermined amount of an active agent of the invention per dose.

For the treatment of the above diseases and/or disorders, the appropriate dosage will vary depending upon, for example, the particular antibody to be employed, the subject treated, the mode of administration and the nature and severity of the condition being treated. In a particular embodiment the liquid pharmaceutical formulation of the invention is administered by intravenous or subcutaneous route. When administered via intravenous injection, it may be administered as a bolus injection or as a continuous infusion. The liquid pharmaceutical formulation according to any of the embodiments of the invention may also be administered by intramuscular injection. The liquid pharmaceutical formulation may be injected using a syringe, an injection device such as an autoinjector, a needleless device, an implant and a patch. The liquid pharmaceutical formulation of the invention may also be administered via inhalation using an inhalation device containing said formulation for such delivery, for example using a nebulizer or liquid inhaler.

The liquid pharmaceutical formulation of the invention is suitably administered to the patient at one time or over a series of treatments and may be administered to the patient at any time from diagnosis onwards; it may be administered as the sole treatment or in conjunction with other drugs or therapies useful in treating the conditions as described herein before.

The antibody or antigen-binding fragment thereof may be the sole active ingredient in the liquid pharmaceutical formulation. Alternatively, the antibody or antigen-binding fragment thereof may be administered in combination, e.g. simultaneously, sequentially or separately, with one or more other therapeutically active ingredients. Active ingredient as employed herein refers to an ingredient with a pharmacological effect, such as a therapeutic effect, at a relevant dose. In some embodiments the antibody or antigen-binding fragment thereof in the liquid pharmaceutical formulation may be accompanied by other active ingredients including other antibodies or non-antibody ingredients. When the antibody in the liquid pharmaceutical formulation according to the invention is an anti-sclerostin antibody, the subject may be administered with an additional active ingredient to treat their bone disorder. The subject may be, for instance, treated with any other therapy for treating bone disorders. In one embodiment, the subject is administered an anti-resorptive, in a particularly preferred instance the additional agent is administered at a time when the subject is not being treated with the liquid pharmaceutical formulation according to the invention and its embodiments. In an alternative embodiment, such an additional active ingredient may be administered at the same time or overlapping with the administration of the liquid pharmaceutical formulation according to the invention. In any embodiment discussed herein, the additional agent may be, for instance, vitamin D. In some embodiments, the other therapeutic active ingredient may be a bone resorption inhibitor. For instance, any suitable anti-resorptive may be employed. In one preferred embodiment, the bone resorption inhibitor is a bisphosphonate, particularly a nitrogen containing bisphosphonate. Examples of bisphosphonates include, but are not limited to, Alendronate, bonefos ciodronate, etidronate, ibandronic acid, olpadronate, neridronate, risedronate sodium, skelid, and zoledronic acid. In another preferred embodiment, the bisphosphonate is zoledronic acid. Bisphosphonates which may be employed include, for instance, Actonel™, Aclasta™/Reclast™, Boniva™/Bonviva™, Fosamax™, and Zometa™. An advantage of alternating between the liquid pharmaceutical formulation comprising an anti-sclerostin antibody and bisphosphonate is that it may help avoid possible side effects arising from the subject being treated with bisphosphonates for a prolonged period. Hence, alternating helps avoid such side-effects, whilst also addressing the problem of resistance developing to the antibody. In a preferred embodiment, the additional active ingredient is an anti-resorptive and even more preferably is Alendronate.

Selected estrogen receptor modulators may also be employed as bone resorption inhibitors, for instance, arzoxifene, bazedoxifene, FC 1271, lasofoxifene, raloxifene, and Tibolone are examples of suitable SERMs. Other bone resorption inhibitors which may be used include estrogen and calcitonin, with examples of calcitonin including salmon calcitonins, such as Miacalcin™.

Strontium compounds, in particular strontium ranelate, or PTH, in particular recombinant parathyroid hormone releasing peptide, parathyroid hormone or analogs thereof (e.g., teriparatide (FORTED®), may also be employed as the bone resorption inhibitor.

In other embodiments, the bone resorption inhibitor is a RANKL inhibitor, such as an anti-RANKL antibody. In one preferred embodiment, the bone resorption inhibitor employed may be denosumab.

In other embodiments the anti-resorptive employed is not a bisphosphonate. Examples, of such agents which may be employed include PROLIA®, calcitonin, and cathepsin K inhibitors (e.g., odanacatib).

In one case, a bone resorption inhibitor may be administered at the same time, or approximately the same time, as the antibody, or so the two therapies overlap. It may be that the bone resorption inhibitor is given to help prolong further the effect of the anti-sclerostin antibody by reducing the breakdown of bone that the antibody has stimulated and in particular where the compound is a bisphosphonate. In one preferred instance, there is no overlap in the treatment of the subject with anti-sclerostin antibody and the further treatment for the bone disorder, for instance the two treatments are alternated, but never overlap.

Antibody molecules may be typically produced by culturing a host cell containing a vector encoding the antibody sequence under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

An antibody or an antigen-binding fragment thereof that can be manufactured according to industrial scales can be produced by culturing eukaryotic host cells transfected with one or more expression vectors encoding the recombinant antibody fragment. The eukaryotic host cells are preferably mammalian cells, more preferably Chinese Hamster Ovary (CHO) cells.

Mammalian cells may be cultured in any medium that will support their growth and expression of the recombinant protein, preferably the medium is a chemically defined medium that is free of animal-derived products such as animal serum and peptone. There are different cell culture mediums available to the person skilled in the art comprising different combinations of vitamins, amino acids, hormones, growth factors, ions, buffers, nucleosides, glucose or an equivalent energy source, present at appropriate concentrations to enable cell growth and protein production. Additional cell culture media components may be included in the cell culture medium at appropriate concentrations at different times during a cell culture cycle that would be known to those skilled in the art.

Mammalian cell culture can take place in any suitable container such as a shake flask or a bioreactor, which may or may not be operated in a fed-batch mode depending on the scale of production required. These bioreactors may be either stirred-tank or air-lift reactors. Various large scale bioreactors are available with a capacity of more than 1,000 L to 50,000 L, preferably between 5,000 L and 20,000 L, or to 10,000 L. Alternatively, bioreactors of a smaller scale such as between 2 L and 100 L may also be used to manufacture an antibody or antibody fragment.

An antibody or antigen-binding fragment thereof is typically found in the supernatant of a mammalian host cell culture, typically a CHO cell culture. For CHO culture processes wherein the protein of interest such as an antibody or antigen-binding fragment thereof is secreted in the supernatant, said supernatant is collected by methods known in the art, typically by centrifugation.

Therefore, the antibody or antigen-binding fragment thereof production method comprises a step of centrifugation and supernatant recovery after cell culture and prior to protein purification. In a further particular embodiment said centrifugation is continuous centrifugation. For avoidance of doubt, supernatant denotes the liquid lying above the sedimented cells resulting from the centrifugation of the cell culture.

Alternatively, host cells are prokaryotic cells, preferably gram-negative bacteria. More preferably, the host cells are E. coli cells. Prokaryotic host cells for protein expression are well known in the art (Terpe, K. Appl Microbiol Biotechnol 72, 211-222 (2006)). The host cells are recombinant cells which have been genetically engineered to produce the protein of interest such as an antigen-binding fragment of an antibody. The recombinant E. coli host cells may be derived from any suitable E. coli strain including from MC4100, TG1, TG2, DHB4, DH5a, DH1, BL21, K12, XL1Blue and JM109. One example is E. coli strain W3110 (ATCC 27,325) a commonly used host strain for recombinant protein fermentations. Antibody fragments can also be produced by culturing modified E. coli strains, for example metabolic mutants or protease deficient E. coli strains.

An antibody fragment is typically found in either the periplasm of the E. coli host cell or in the host cell culture supernatant, depending on the nature of the protein, the scale of production and the E. coli strain used. The methods for targeting proteins to these compartments are well known in the art (Makrides, S. C.; Microbiol Rev 60, 512-538 (1996)). Examples of suitable signal sequences to direct proteins to the periplasm of E. coli include the E. coli PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the co-expression of bacteriocin release protein, the mitomycin-induced bacteriocin release protein along with the addition of glycine to the culture medium and the co-expression of the kil gene for membrane permeabilization. Most preferably, the recombinant protein is expressed in the periplasm of the host E. coli.

Expression of the recombinant protein in the E. coli host cells may also be under the control of an inducible system, whereby the expression of the recombinant antibody in E. coli is under the control of an inducible promoter. Many inducible promoters suitable for use in E. coli are well known in the art and depending on the promoter expression of the recombinant protein can be induced by varying factors such as temperature or the concentration of a particular substance in the growth medium. Examples of inducible promoters include the E. coli lac, tac, and trc promoters which are inducible with lactose or the non-hydrolyzable lactose analog, isopropyl-b-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose.

E. coli host cell cultures (fermentations) may be cultured in any medium that will support the growth of E. coli and expression of the recombinant protein. The medium may be any chemically defined medium such as e.g. described in Durany O, et al. (2004). Studies on the expression of recombinant fuculose-1-phosphate aldolase in Escherichia coli. Process Biochem 39, 1677-1684.

Culturing of the E. coli host cells can take place in any suitable container such as a shake flask or a fermenter depending on the scale of production required. Various large scale fermenters are available with a capacity of more than 1,000 liters up to about 100,000 liters. Preferably, fermenters of 1,000 to 50,000 liters are used, more preferably 1,000 to 25,000, 20,000, 15,000, 12,000 or 10,000 liters. Smaller scale fermenters may also be used with a capacity of between 0.5 and 1,000 liters.

Fermentation of E. coli may be performed in any suitable system, for example continuous, batch or fed-batch mode depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete. Fed-batch mode may also be used pre-induction to control the metabolism of the E. coli host cells and to allow higher cell densities to be reached.

If desired, the host cells may be subject to collection from the fermentation medium, e.g. host cells may be collected from the sample by centrifugation, filtration or by concentration. In this case the process typically comprises a step of centrifugation and cell recovery prior to extracting the protein.

For *E. coli* fermentation processes wherein the protein of interest such as an antibody or antigen-binding fragment of an antibody is found in the periplasmic space of the host cell it is required to release the protein from the host cell. The release may be achieved by any suitable method such as cell lysis by mechanical or pressure treatment, freeze-thaw treatment, osmotic shock, extraction agents or heat treatment. Such extraction methods for protein release are well known in the art. Therefore in a particular embodiment, the production process comprises an additional protein extraction step prior to protein purification.

Other methods for obtaining antigen-binding fragment of a human antibody in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art. Human antibodies may also be generated from isolated human B cells that are ex vivo immunized with an antigen of interest and subsequently fused to generate hybridomas which can then be screened for the optimal human antibody.

EXAMPLES

Example 1: Hydroxypropyl-Gamma-Cyclodextrin (HPGCD) Screening

Stability and propensity to precipitate within a formulation is greatly affected by the concentration (steric crowding) and the excipients used within the formulation to control the interactions observed due to steric crowding.

In order to determine whether HPGCD has an impact on the precipitation profile at physiological pH, basic formulation of romosozumab (pI 6.9) at a concentration of 120 mg/mL with and without HPGCD were run through the pH shift model.

The pH shift model is designed to replicate the pH shift that occurs when a formulation comprising a drug is administered by subcutaneous injection (Elena Garcia-Fruitós, Insoluble Proteins: Methods and Protocols, Methods in Molecular Biology, vol. 1258, Chapter 18:321-330, Springer Science+Business Media New York (2015)). Biotherapeutic proteins, in particular antibodies, are often formulated below physiological pH (~pH7.0). If the pI of the protein is less than pH 7.0 but higher than the formulation pH, the protein will shift through its pI. This will reduce the solubility of the protein and cause it to precipitate. This model is designed to replicate this pH shift and aid in assessing formulations' suitability for subcutaneous injection.

The model is run over 24 hours. A tissue buffer (10 mM Sodium Bicarbonate and 150 mM Sodium Chloride) is prepared the day before and placed into the $CO_2$ incubator at 37° C./7% $CO_2$ on a gentle stir overnight to equilibrate. About 0.5 mL of each test sample is loaded into a slide-a-lyser cassette according to the manufacturer instructions (Thermo Scientific, Slide-A-Lyzer Dialysis Cassettes G2, Prod #87727, 7000 MWCO, 0.5 mL). The slide-a-lyser cassettes are gently placed into the equilibrated tissue buffer within the $CO_2$ incubator and left overnight. The slide-a-lyser cassettes are visually assessed against a white and black background for signs of precipitation every hour for the first 4-6 hours and then after 24 hours (or longer).

Romosozumab at 120 mg/mL in 50 mM sodium acetate, 14 mM calcium acetate, 6% sucrose, 0.006% polysorbate 20 at pH 5.2 (drug solution, DS) were prepared by performing a 1:1 serial dilution. An initial solution was prepared by adding 881 mg of HPGCD to 2 ml of romosozumab at 120 mg/mL in DS to give a final HPGCD concentration of 250 mM. Half of this solution (1 mL) was mixed 1:1 with the same volume of romosozumab at 120 mg/mL in DS to achieve a sample of romosozumab at 120 mg/mL in DS with 125 mM HPGCD. This process was repeated to achieve samples of romosozumab at 120 mg/mL in DS with 62.5 mM, 31.25 mM, 15.63 mM and 7.8 mM HPGCD. Romosozumab at 120 mg/mL in DS was used as the control.

The formulations comprising 0 to 250 mM concentrations of HPGCD were buffer exchanged and concentrated using 30 kDa Sartorius Viva Spin centrifugal spin filters of varying volumes (2-20 mL). The spin tubes were centrifuged at 3000 rpm, 5° C. for ≤60 minutes. Samples were mixed between spin cycles using a positive displacement pipette≥5× volume exchange.

The concentration of each sample was measured in duplicate before and after dialysis (Table 2) using the C Technologies Solo VPE high concentration UV spectrophotometer linked to a Cary 50 spectrophotometer. Concentration was determined by absorbance at Å280. Result reported as mean of duplicate sample readings. The pH was determined using the Hach H260G pH meter and ISFET solid state probe. All samples were stored at 5° C. after preparation.

TABLE 2

| Sample | Replicates | | Mean | SD | % CV |
|---|---|---|---|---|---|
| | 1 | 2 | | | |
| Pre-dialysis | | | | | |
| 0 mM HPGCD | 122.18 | 120.58 | 121.38 | 1.13 | 0.93 |
| 7.8 mM HPGCD | 120.15 | 120.60 | 120.38 | 0.32 | 0.26 |
| 15.6 mM HPGCD | 122.61 | 120.80 | 121.71 | 1.28 | 1.05 |
| 31.3 mM HPGCD | 118.52 | 119.04 | 118.79 | 0.36 | 0.31 |
| 62.5 mM HPGCD | 114.86 | 115.69 | 115.28 | 0.59 | 0.51 |
| 125 mM HPGCD | 109.36 | 109.20 | 109.29 | 0.11 | 0.10 |
| 250 mM HPGCD | 96.77 | 96.82 | 96.8 | 0.03 | 0.03 |
| Post-dialysis | | | | | |
| 0 mM HPGCD | 29.18 | 28.99 | 29.1 | 0.13 | 0.45 |
| 7.8 mM HPGCD | 29.42 | 27.66 | 28.5 | 1.24 | 4.35 |
| 15.6 mM HPGCD | 26.89 | 26.78 | 26.8 | 0.08 | 0.29 |
| 31.3 mM HPGCD | 27.25 | 27.35 | 27.3 | 0.07 | 0.26 |
| 62.5 mM HPGCD | 28.98 | 28.78 | 28.9 | 0.14 | 0.49 |
| 125 mM HPGCD | — | — | — | — | — |
| 250 mM HPGCD | — | — | — | — | — |

Visual assessment of the sample was performed each hour for the first five hours and after 72 hours. Results are reported in Table 3. Addition of HPGCD reduces the rate of precipitation.

TABLE 3

| | Precipitation Assessment | | | | | | |
|---|---|---|---|---|---|---|---|
| Time (hr) | 0 mM HPGCD | 7.8 mM HPGCD | 15.6 mM HPGCD | 31.3 mM HPGCD | 62.5 mM HPGCD | 125 mM HPGCD | 250 mM HPGCD |
| 0 | No | No | No | No | No | No | No |
| 1 | Light | Light | Light | Light | No | No | No |
| 2 | Moderate | Moderate | Moderate | Moderate | Light | No | No |
| 3 | Heavy | Heavy | Heavy | Heavy | Moderate | No | No |
| 4 | Heavy | Heavy | Heavy | Heavy | Moderate | Light | No |
| 5 | Heavy | Heavy | Heavy | Heavy | Heavy | Light | No |
| 72 | Heavy | Heavy | Heavy | Heavy | Heavy | Moderate | Light |

Example 2: Methionine Screening

Once the impact of HPGCD on the precipitation profile of the basic romosozumab formulation of example 1 was assessed, the effect of methionine was investigated.

In order to determine whether methionine has an impact on the precipitation profile at physiological pH, basic formulations of romosozumab (pI 6.9) at a concentration of 90 mg/ml (control only) 120 mg/mL or 180 mg/ml with (55 mM and 200 mM) and without methionine were run through the pH shift model described in example 1.

Romosozumab in 50 mM sodium acetate, 14 mM calcium acetate, 6% sucrose, 0.006% polysorbate 20 at pH 5.2 (drug solution, DS) was concentrated to 125 mg/mL or to 190 mg/mL using 30 kDa Sartorius Viva Spin centrifugal spin filters. The spin tubes were centrifuged at 3000 rpm, 5° C. for 60 minutes; samples were mixed between spin cycles using a positive displacement pipette.

The required amount of methionine to produce 2.2 mL of sample with the required concentration (55 and 200 mM) was weighed (0.018 g and 0.0066 g, respectively) using an analytical balance. Methionine was dissolved in 2.2 mL of the appropriate protein solution (125 mg/mL or 190 mg/mL).

The concentration of each sample was measured in duplicate before and after dialysis (Table 4) using the C Technologies Solo VPE high concentration UV spectrophotometer linked to a Cary 50 spectrophotometer. Concentration was determined by absorbance at Å280. Result reported as mean of duplicate sample readings.

TABLE 4

| | Replicates | | | | |
|---|---|---|---|---|---|
| Sample | 1 | 2 | Mean | SD | % CV |
| Pre-dialysis | | | | | |
| 120 mg/mL 55 mM Meth | 122.39 | 124.35 | 123.38 | 1.39 | 1.12 |
| 120 mg/mL 200 mM Meth | 121.81 | 124.43 | 123.13 | 1.85 | 1.51 |
| 180 mg/mL 55 mM Meth | 188.84 | 187.96 | 188.40 | 0.62 | 0.33 |
| 180 mg/mL 200 mM Meth | 186.70 | 186.69 | 186.70 | 0.01 | 0.00 |
| 90 mg/mL Control | 90.93 | 91.32 | 91.13 | 0.27 | 0.30 |
| 120 mg/mL Control | 118.18 | 119.16 | 118.67 | 0.69 | 0.58 |
| 180 mg/mL Control | 182.90 | 183.31 | 183.11 | 0.29 | 0.16 |
| Post-dialysis | | | | | |
| 120 mg/mL 55 mM Meth | 24.64 | 24.57 | 24.61 | 0.05 | 0.22 |
| 120 mg/mL 200 mM Meth | 24.38 | 24.41 | 24.40 | 0.01 | 0.08 |
| 180 mg/mL 55 mM Meth | 31.39 | 31.58 | 31.49 | 0.13 | 0.42 |
| 180 mg/mL 200 mM Meth | 30.75 | 30.57 | 30.66 | 0.12 | 0.40 |
| 90 mg/mL Control | 22.51 | 22.60 | 22.56 | 0.06 | 0.28 |
| 120 mg/mL Control | 23.54 | 23.57 | 23.56 | 0.02 | 0.10 |
| 120 mg/mL Control | 31.47 | 31.30 | 31.39 | 0.12 | 0.39 |

The pH of the formulations pre-dialysis and after 24 h, measured using the Hach H260G pH meter and ISFET solid state probe, confirmed the pH shift (Table 5).

TABLE 5

| | pH | | Viscosity | Osmolality |
|---|---|---|---|---|
| Sample | t0 | t24 | (cP) | (mOsmol) |
| 120 mg/mL 55 mM Meth | 5.14 | 7.80 | 5.21 | 392 |
| 120 mg/mL 200 mM Meth | 5.28 | 7.81 | 5.55 | 573 |
| 180 mg/mL 55 mM Meth | 5.23 | 7.75 | 34.36 | 508 |
| 180 mg/mL 200 mM Meth | 5.23 | 7.73 | 29.56 | 712 |
| 90 mg/mL Control | 5.27 | 7.86 | 2.55 | 321 |
| 120 mg/mL Control | 5.22 | 7.80 | 4.76 | 320 |
| 180 mg/mL Control | 5.28 | 7.77 | 27.21 | 398 |
| Tissue buffer | 6.99 | | | |

Visual assessment of the sample was performed each hour for the first four hours. Results are reported in Table 6.

TABLE 6

| Time (hr) | 120 mg/mL 55 mM Meth | 120 mg/mL 200 mM Meth | 180 mg/mL 55 mM Meth | 180 mg/mL 200 mM Meth | 90 mg/mL Control | 120 mg/mL Control | 180 mg/mL Control |
|---|---|---|---|---|---|---|---|
| 0 | No | No | No | No | No | No | No |
| 1 | Light | Light | Heavy | Heavy | Very Light | Light | Moderate |
| 2 | Heavy | Heavy | Very Heavy | Very Heavy | Moderate | Moderate | Very Heavy |
| 3 | Heavy | Heavy | Very Heavy | Very Heavy | Heavy | Heavy | Very Heavy |
| 4 | Heavy | Heavy | Very Heavy | Very Heavy | Heavy | Heavy | Very Heavy |

As can be observed by the results reported in Table 6, the addition of methionine alone did not alter the rate of precipitation.

Example 3: Combination of HPGCD and Methionine Screening

Once assessed the impact of HPGCD alone or methionine alone on the precipitation profile of the basic romosozumab formulation of example 1, the combined effect of HPGCD and methionine was investigated.

Romosozumab in 50 mM sodium acetate, 14 mM calcium acetate, 6% sucrose, 0.006% polysorbate 20 at pH 5.2 (drug solution, DS) was concentrated to 125 mg/mL or to 190 mg/mL using 30 kDa Sartorius Viva Spin centrifugal spin filters. The spin tubes were centrifuged at 3000 rpm, 5° C. for ≤60 minutes; samples were mixed between spin cycles using a positive displacement pipette.

The required amount of methionine to produce 2.2 mL of sample with the required concentration (55 and 200 mM) was weighed (0.018 g and 0.066 g, respectively) using an analytical balance. The Methionine was dissolved in 2.2 mL of the appropriate protein solution (125 mg/mL or 190 mg/mL). The required amount of HPGCD to produce 1 mL of 30 mM HPGCD at the required concentration was weighed (0.053 g) using an analytical balance. 1 ml of the appropriate protein/methionine solution was used to dissolve the HPGCD.

The formulations were buffer exchanged and concentrated as previously described in examples 1 and 2. The concentration of each sample was measured in duplicate before and after dialysis (Table 7) as previously described in examples 1 and 2. Results are reported as mean of duplicate sample readings.

TABLE 7

| Sample | Replicates 1 | 2 | Mean | SD | % CV |
|---|---|---|---|---|---|
| Pre-dialysis ||||||
| 120 mg/mL 55 mM Meth + 30 mM HPGCD | 118.83 | 121.55 | 120.19 | 1.92 | 1.60 |
| 120 mg/mL 200 mM Meth + 30 mM HPGCD | 118.63 | 119.00 | 118.82 | 0.26 | 0.22 |
| 180 mg/mL 55 mM Meth + 30 mM HPGCD | 184.44 | 185.70 | 185.08 | 0.89 | 0.48 |
| 180 mg/mL 200 mM Meth + 30 mM HPGCD | 182.84 | 181.63 | 182.24 | 0.86 | 0.47 |
| 90 mg/mL Control | 90.93 | 91.32 | 91.13 | 0.27 | 0.30 |
| 120 mg/mL Control | 118.18 | 119.16 | 118.67 | 0.69 | 0.58 |
| 180 mg/mL Control | 182.90 | 183.31 | 183.11 | 0.29 | 0.16 |

TABLE 7-continued

| Sample | Replicates 1 | 2 | Mean | SD | % CV |
|---|---|---|---|---|---|
| Post-dialysis ||||||
| 120 mg/mL 55 mM Meth + 30 mM HPGCD | 21.65 | 21.61 | 21.63 | 0.02 | 0.11 |
| 120 mg/mL 200 mM Meth + 30 mM HPGCD | 21.23 | 21.34 | 21.29 | 0.07 | 0.36 |
| 180 mg/mL 55 mM Meth + 30 mM HPGCD | 27.37 | 27.66 | 27.52 | 0.20 | 0.74 |
| 180 mg/mL 200 mM Meth + 30 mM HPGCD | 26.63 | 26.48 | 26.56 | 0.11 | 0.41 |
| 90 mg/mL DS | 22.51 | 22.60 | 22.56 | 0.06 | 0.28 |
| 120 mg/mL DS | 23.54 | 23.57 | 23.56 | 0.02 | 0.10 |
| 120 mg/mL DS | 31.47 | 31.30 | 31.39 | 0.12 | 0.39 |

The pH of the formulations pre-dialysis and after 24 h confirmed the pH shift (Table 8).

TABLE 8

| Sample | pH t0 | pH t24 | Viscosity (cP) | Osmolality (mOsmol) |
|---|---|---|---|---|
| 120 mg/mL 55 mM Meth + 30 mM HPGCD | 5.19 | 7.80 | 6.56 | 486 |
| 120 mg/mL 200 mM Meth + 30 mM HPGCD | 5.24 | 7.75 | 7.09 | 672 |
| 180 mg/mL 55 mM Meth + 30 mM HPGCD | 5.19 | 7.76 | 41.62 | 621 |
| 180 mg/mL 200 mM Meth + 30 mM HPGCD | 5.28 | 7.66 | 37.07 | 862 |
| 90 mg/mL Control | 5.27 | 7.86 | 2.55 | 321 |
| 120 mg/mL Control | 5.22 | 7.80 | 4.76 | 320 |
| 180 mg/mL Control | 5.28 | 7.77 | 27.21 | 398 |
| Tissue buffer* | 6.99 | | | |

Visual assessment of the sample was performed each hour for the first four hours. Results are reported in Table 9.

TABLE 9

| Time (hr) | 120 mg/mL 55 mM Meth + 30 mM HPGCD | 120 mg/mL 200 mM Meth + 30 mM HPGCD | 180 mg/mL 55 mM Meth + 30 mM HPGCD | 180 mg/mL 200 mM Meth + 30 mM HPGCD | 90 mg/mL Control | 120 mg/mL Control | 180 mg/mL Control |
|---|---|---|---|---|---|---|---|
| 0 | No | No | No | No | No | No | No |
| 1 | Light | Very Light | Heavy | Moderate | Very Light | Light | Moderate |
| 2 | Heavy | Moderate | Heavy | Heavy | Moderate | Moderate | Very Heavy |
| 3 | Heavy | Heavy | Heavy | Heavy | Heavy | Heavy | Very Heavy |
| 4 | Heavy | Heavy | Heavy | Heavy | Heavy | Heavy | Very Heavy |

The addition of HPGCD and methionine improved the rate of precipitation over the basic formulation, especially at high concentrations of romosozumab (180 mg/mL).

Example 4: Extended Methionine and HPGCD Screening and Effects on Osmolality and Viscosity Twenty different formulations comprising combinations of HPGCD and methionine with and without calcium acetate were made in order to investigate the additional concentrations of methionine and HPGCD and their effect on the pH, viscosity and osmolality.

Romosozumab at 120 mg/mL in 50 mM sodium acetate, 14 mM calcium acetate, 6% sucrose, 0.006% polysorbate 20 at pH 5.2 (drug solution, DS) was concentrated to ~190 mg/mL using 30 kDa Sartorius Viva Flow 50, bench scale tangential flow filtration (TFF) cartridge. System was run using a Masterflex peristaltic pump at a pressure of ~2.5 Bar, ≥6× volume exchange.

Romosozumab at 120 mg/mL in DS was buffer exchanged to 55 mM sodium acetate, 6% sucrose, 0.006% polysorbate 20, pH5.2 (without calcium acetate) and concentrated to ~190 mg/mL using 30 kDa Sartorius Viva Flow 50, bench scale tangential flow filtration (TFF) cartridge. System was run using a Masterflex peristaltic pump at a pressure of ~2.5 Bar, ≥6× volume exchange.

Methionine and HPGCD were spiked according to the experiment design (Table 10).

TABLE 10

| HPGCD mM | Weight (g) | Methionine mM | Weight (g) |
|---|---|---|---|
| 30 | 0.0529 | 55 | 0.0098 |
| 77.5 | 0.1366 | 127.5 | 0.0228 |
| 125 | 0.2203 | 200 | 0.0358 |
| MW | 1762 g/mol | MW | 149.21 g/mol |
| Volume | 1 ml | Volume | 1.2 ml |

The required amount of Methionine to produce 1.2 mL of sample with the required concentration was weighed using an analytical balance. The Methionine was dissolved in 2.2 mL of the appropriate protein solution (with/without calcium acetate). The required amount of HPGCD to produce 1 mL of sample at the required concentration was weighed using an analytical balance. 1 ml of the appropriate protein/methionine solution (with/without calcium acetate) was used to dissolve the HPGCD.

Samples were run through the pH shift model. The pH and the concentrations were measure pre- and post-dialysis as described above. Pre-dialysis osmolality and viscosity were also measured in order to identify specific formulations which would meet the physiological requirements for subcutaneous administration. Table 11 shows the 20 newly designed formulations and the 6 controls run in this experiment.

TABLE 11

| Formulation # | HPGCD (mM) | Met (mM) | Ca (14 mM) | Concentration (mg/mL) Mean | Viscosity (cP) | Osmolality (mOsmol) | pH t0 | pH t24 |
|---|---|---|---|---|---|---|---|---|
| 1 | 77.5 | 55 | No | 154.1 | — | 773.0 | 5.17 | 8.08 |
| 2 | 30 | 200 | Yes | 175.8 | 36.3 | 804.0 | 5.03 | 7.99 |
| 3 | 77.5 | 127.5 | Yes | 171.7 | 51.9 | 930.0 | 5.02 | 8.01 |
| 4 | 30 | 127.5 | No | 157.6 | 34.1 | 674.0 | 5.04 | 7.97 |
| 5 | 77.5 | 127.5 | Yes | 169.8 | 51.1 | 896.7 | 4.99 | 7.96 |
| 6 | 77.5 | 200 | No | 148.7 | 36.0 | 988.3 | 5.15 | 8.02 |
| 7 | 77.5 | 55 | No | 151.1 | 41.2 | 752.3 | 5.31 | 8.01 |
| 8 | 77.5 | 200 | No | 148.9 | 36.3 | 986.0 | 5.3 | 8.01 |
| 9 | 125 | 200 | Yes | 160.0 | 66.4 | 1305.5 | 5.25 | 8.08 |
| 10 | 30 | 55 | Yes | 178.4 | 36.5 | 590.3 | 5.32 | 8.05 |
| 11 | 77.5 | 127.5 | Yes | 174.0 | 51.8 | 908.3 | 5.2 | 8.00 |
| 12 | 30 | 127.5 | No | 160.4 | 27.5 | 654.0 | 5.13 | 8.04 |
| 13 | 125 | 55 | Yes | 167.7 | 73.2 | 1043.0 | 5.17 | 8.03 |
| 14 | 125 | 127.5 | No | 146.7 | 50.6 | 1149.0 | 5.22 | 8.05 |
| 15 | 125 | 127.5 | No | 146.8 | 52.4 | 1165.3 | 5.23 | 8.28 |
| 16 | 125 | 127.5 | Yes | 167.0 | 69.4 | 1198.0 | 5.18 | 8.04 |
| 17 | 77.5 | 55 | Yes | 177.5 | 53.3 | 819.0 | 5.15 | 8.15 |
| 18 | 77.5 | 200 | Yes | 173.5 | 48.6 | 1043.3 | 5.2 | 8.15 |
| 19 | 30 | 127.5 | Yes | 183.2 | 39.6 | 681.3 | 5.14 | 8.08 |
| 20 | 77.5 | 127.5 | No | 153.0 | 41.8 | 897.0 | 5.27 | 8.11 |

TABLE 11-continued

| Formulation # | HPGCD (mM) | Met (mM) | Ca (14 mM) | Concentration (mg/mL) Mean | Viscosity (cP) | Osmolality (mOsmol) | pH t0 | pH t24 |
|---|---|---|---|---|---|---|---|---|
| 21 | 0 | 0 | Yes | 90.4 | 2.8 | 328.7 | 5.06 | 8.22 |
| 22 | 0 | 0 | Yes | 118.8 | 5.4 | 323.7 | 5.18 | 8.19 |
| 23 | 0 | 0 | Yes | 184.3 | 32.2 | 388.7 | 5.14 | 8.16 |
| 24 | 0 | 0 | No | 93.4 | 2.83 | 322.0 | 5.18 | 8.26 |
| 25 | 0 | 0 | No | 123.7 |  | 336.7 | 5.21 | 8.18 |
| 26 | 0 | 0 | Yes | 187.4 | 39.5 | 395.0 | 5.37 | 8.13 |

The concentrations of the formulations pre-dialysis were measured and are shown in Table 11, fifth column; the post-dialysis concentrations were also measured and their trends were similar to those of formulations previously tested (data not shown). Pre- and post-dialysis pH, viscosity and osmolality were measured and are also illustrated in Table 11.

Visual assessment of the sample was performed each hour for the first five hours. Results are reported in Table 12.

before concentration. Concentrations were measured using the Solo VPE high concentration UV spectrophotometer. Romosozumab Extinction Coefficient used was 1.50 ml/(mg*cm). Concentration was determined from duplicate readings. Buffer exchange and concentrations were performed in a VivaSpin Spin 20, 30 KD centrifugal spin filters using the centrifuge in 1 hour blocks at 3200 rpm, 5° C. The material was mixed using a positive displacement pipette between each spin. Samples were prepared in duplicate. After 20 spins all 6 volumes of buffer were added to perform

TABLE 12

| hr | 1 | 2 | 3 | 4 | 5 | 6 | 7 | 8 | 9 | 10 | 11 | 12 | 13 |
|---|---|---|---|---|---|---|---|---|---|---|---|---|---|
| 0 | No | No | No | No | No | No | No | No | No | No | No | No | No |
| 1 | Very Heavy | Light | Very Light | Very Heavy | Very Light | Moderate | Very Heavy | Moderate | No | Light | Heavy | Light | Very Heavy | Moderate |
| 2 | Very Heavy | Moderate | Moderate | Very Heavy | Moderate | Heavy | Very Heavy | Heavy | Moderate | Very Heavy | Moderate | Very Heavy | Heavy |
| 3 | Very Heavy | Heavy | Heavy | Very Heavy | Moderate | Heavy | Very Heavy | Heavy | Moderate | Very Heavy | Heavy | Very Heavy | Heavy |
| 4 | Very Heavy | Heavy | Heavy | Very Heavy | Heavy | Heavy | Very Heavy | Very Heavy | Moderate | Very Heavy | Very Heavy | Very Heavy | Very Heavy |
| 5 | Very Heavy | Very Heavy | Very Heavy | Very Heavy | Very Heavy | Very Heavy | Very Heavy | Very Heavy | Heavy | Very Heavy | Very Heavy | Very Heavy | Very Heavy |

| hr | 14 | 15 | 16 | 17 | 18 | 19 | 20 | 21 | 22 | 23 | 24 | 25 | 26 |
|---|---|---|---|---|---|---|---|---|---|---|---|---|---|
| 0 | No | No | No | No | No | No | No | No | No | No | No | No | No |
| 1 | Very Heavy | Very Heavy | Light | Moderate | Moderate | Heavy | Heavy | No | Light | Very Heavy | Moderate | Heavy | Very Heavy |
| 2 | Very Heavy | Very Heavy | Moderate | Heavy | Moderate | Very Heavy | Very Heavy | Light | Moderate | Very Heavy | Heavy | Very Heavy | Very Heavy |
| 3 | Very Heavy | Very Heavy | Moderate | Heavy | Heavy | Very Heavy | Very Heavy | Moderate | Heavy | Very Heavy | Heavy | Very Heavy | Very Heavy |
| 4 | Very Heavy | Very Heavy | Heavy | Very Heavy | Heavy | Very Heavy | Very Heavy | Heavy | Heavy | Very Heavy | Heavy | Very Heavy | Very Heavy |
| 5 | Very Heavy | Very Heavy | Heavy | Very Heavy | Very Heavy | Very Heavy | Very Heavy | Heavy | Very Heavy | Very Heavy | Heavy | Very Heavy | Very Heavy |

All results were entered into statistical analysis package (Software SAS JMP 11, version 11.0.0; 64 bit). Four formulations (details in Table 13, second column) were selected for further testing for having predicted osmolalities (~800 mOsml up to ~1000 mOsmol) and viscosities (<80 cP) suitable for desired pharmaceutical formulations.

To prepare the formulation comprising HPGCD and Methionine, it was required to buffer exchange and concentrate romosozumab from ~119 mg/mL to ~150 mg/mL and to ~180 mg/ml; 6× volume buffer exchanges was performed the buffer exchange. Concentration of ~150 mg/mL and ~180 mg/mL were achieved for formulations B, C and D.

Due to issue to concentrate formulation A, it was decided to use capillary to concentrate this formulation and attain a concentration of 150 mg/mL and then one of 180 mg/ml. All material was sterile filtered using a 0.22 mm syringe filter and stored at 5° C. after preparation. Each sample was spiked with the corresponding 1% polysorbate 20 to a concentration of 0.006%. All formulations were within ±5% of target concentration (Table 13).

TABLE 13

| Formulation # | Details | Required concentration | Final Concentration | Predicted Osmolality (mOsmol) | Predicted Viscosity (cP) |
|---|---|---|---|---|---|
| A | 55 mM NaACE*, 14 mM CaACE#, 6% sucrose, 0.006% polysorbate 20, 96 mM HPGCD, pH 5.2 | 150 | 148.30 | 772.8 | 52.6 |
|   |   | 180 | 176.87 | 800.4 | 64.6 |
| B | 55 mM NaACE*, 14 mM CaACE#, 6% sucrose, 0.006% polysorbate 20, 78 mM HPGCD, 55 mM Methionine pH 5.2 | 150 | 152.25 | 773.5 | 42.8 |
|   |   | 180 | 182.12 | 801.1 | 54.8 |
| C | 55 mM NaACE*, 14 mM CaACE#, 6% sucrose, 0.006% polysorbate 20, 55 mM HPGCD, 125 mM Methionine pH 5.2 | 150 | 151.02 | 771.5 | 33.1 |
|   |   | 180 | 186.24 | 799.1 | 45.1 |
| D | 55 mM NaACE*, 14 mM CaACE#, 6% sucrose, 0.006% polysorbate 20, 80 mM HPγCD, 160 mM Methionine pH 5.2 | 150 | 151.21 | 955.3 | 40.5 |
|   |   | 180 | 183.48 | 982.9 | 52.3 |

*NaACE = Sodium Acetate;
CaACE = Calcium Acetate

The concentrations of these formulations were measured post-dialysis and concentrations were as expected following the same trends as for formulations previously tested (data not shown). The pre- and post-dialysis pHs of each of the formulations were measured along with the viscosities and osmolalities pre-dialysis and these results are reported in Table 14. In Table 14, A150 means formulation A as of Table 12 with 150 mg/mL of romosozumab, A180 means formulation A as of Table 13 with 180 mg/mL of romosozumab etc. Control formulations comprise the basic formulation of 55 mM sodium acetate, 14 mM calcium acetate, 6% sucrose, 0.006% polysorbate 20, 96 mM HPGCD, pH 5.2 at concentration of romosozumab of 90 mg/mL, 120 mg/mL, 150 mg/mL and 180 mg/mL.

TABLE 14

| Formulation | pH t0 | pH t24 | Viscosity (cP) | Osmolality (mOsmol) |
|---|---|---|---|---|
| A 150 | 5.55 | 7.94 | 164.41 | 1680 |
| A 180 | # | 8.12 | # | # |
| B 150 | 5.61 | 8.05 | 133.16 | 748 |
| B 180 | 5.57 | 8.02 | 594.17 | # |
| C 150 | 5.48 | 7.96 | 83.00 | 747 |
| C 180 | 5.65 | 7.99 | 343.54 | 847 |
| D 150 | 5.64 | 7.99 | 162.55 | 853 |
| D 180 | 5.71 | 8.03 | 765.78 | # |
| Control 90 | 5.28 | 8.03 | 3.19 | 323 |
| Control 120 | 5.22 | 7.99 | 6.09 | 326 |
| Control 150 | 5.26 | 7.97 | 13.08 | 354 |
| Control 180 | 5.26 | 7.99 | 27.2 | 386 |
| Tissue Buffer | 7.17 | 7.15 |   |   |

# = not enough sample to test

In summary, the combination of HPGCD and methionine has been found to be surprisingly beneficial for stabilizing antibodies, especially at high concentrations, in liquid formulations.

The invention claimed is:

1. A liquid pharmaceutical formulation comprising:
   a. an antibody or an antigen-binding fragment thereof as an active ingredient, wherein the antibody or antigen-binding fragment thereof comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6, wherein the antibody or antigen-binding fragment thereof is present in the liquid formulation at a concentration ranging from 90 mg/ml to 180 mg/ml;
   b. cyclodextrin at a concentration ranging from 7.5 mM to 250 mM and
   c. an amino acid consisting of methionine, wherein the methionine is present in the formulation at a concentration ranging from 7.5 mM to 200 mM.

2. The liquid formulation according to claim 1, wherein the antibody is a human or humanised antibody or antigen-binding fragment thereof.

3. The liquid formulation according to claim 1, wherein:
   a. the antibody or the antigen-binding fragment thereof has a light variable region having the sequence as defined in SEQ ID NO: 7 and a heavy variable region having the sequence as defined in SEQ ID NO: 8; or
   b. the antibody has
      i. a light chain having the sequence as defined in SEQ ID NO: 9 and a heavy chain having the sequence as defined in SEQ ID NO: 10; or ii. a light chain having the sequence as defined in SEQ ID NO: 11 and a heavy chain having the sequence as defined in SEQ ID NO: 12.

4. The liquid formulation according to claim 1, wherein the antibody is romosozumab.

5. The liquid formulation according to claim 1 having a pH of from 4.0 to 7.5.

6. The liquid formulation according to claim 1 wherein the cyclodextrin is selected from alpha-cyclodextrin, beta-cyclodextrin, dimethyl-beta-cyclodextrin, trimethyl-beta-cyclodextrin, randomly methylated beta-cyclodextrin, hydroxyethyl-beta-cyclodextrin, hydroxypropyl-beta-cyclodextrin (i.e. 2 hydroxypropyl-beta-cyclodextrin, 3-hydroxypropyl-beta-cyclodextrin or 2,3-dihydroxypropyl-beta-cyclodextrin), hydroxyisobutyl-beta-cyclodextrin sulfobutylether beta-cyclodextrin, glucosyl-beta-cyclodextrin, maltosyl-beta-cyclodextrin, gamma-cyclodextrin, hydroxypropyl-gamma-cyclodextrin (i.e. 2 hydroxypropyl-gamma-cyclodextrin, 3-hydroxypropyl-gamma-cyclodextrin or 2,3-dihydroxypropyl-gamma-cyclodextrin), cyclodextrin-containing polymers or combinations thereof.

7. The liquid formulation according to claim 6, wherein the cyclodextrin is selected from hydroxypropyl-gamma-cyclodextrin.

8. The liquid formulation according to claim 1, wherein the formulation comprises from 90 mg/ml to 180 mg/ml of antibody, from 10 mM to 55 mM sodium acetate, from 0 to 14 mM calcium acetate, from 0 to 6% sucrose, from 0 to 0.006% polysorbate 20, from 55 mM to 80 mM hydroxypropyl-gamma-cyclodextrin, from 55 mM to 160 mM methionine at pH 5.2.

9. The liquid formulation according to claim 8, wherein the antibody is romosozumab.

10. The liquid formulation according to claim 1 wherein the liquid formulation is not a hydrogel.

11. The liquid formulation according to claim 1 wherein the liquid formulation comprises at least 2% water.

12. The liquid formulation according to claim 8, wherein the formulation comprises from 120 mg/ml to 180 mg/ml of romosozumab.

* * * * *

SEQUENCE LISTING

<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: CDR-H1

<400> SEQUENCE: 1

Asp Tyr Asn Met His
1               5

<210> SEQ ID NO 2
<211> LENGTH: 17
<212> TYPE: PRT
<213> ORGANISM: Artificial Sequence -continued

```
<220> FEATURE:
<223> OTHER INFORMATION: CDR-H2

<400> SEQUENCE: 2

Glu Ile Asn Pro Asn Ser Gly Gly Ala Gly Tyr Asn Gln Lys Phe Lys
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: CDR-H3

<400> SEQUENCE: 3

Leu Gly Tyr Asp Asp Ile Tyr Asp Asp Trp Tyr Phe Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CDR-L1

<400> SEQUENCE: 4

Arg Ala Ser Gln Asp Ile Ser Asn Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDR-L2

<400> SEQUENCE: 5

Tyr Thr Ser Arg Leu Leu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR-L3

<400> SEQUENCE: 6

Gln Gln Gly Asp Thr Leu Pro Tyr Thr
1               5

<210> SEQ ID NO 7
<211> LENGTH: 107
<212> TYPE: PRT
<213> ORGANISM: Artificial Sequence
<220> FEATURE:
<223> OTHER INFORMATION: Light variable region

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30
```

Leu Asn Trp Tyr Gln Gln Lys Pro Gly Lys Ala Pro Lys Leu Leu Ile
            35                  40                  45

Tyr Tyr Thr Ser Arg Leu Leu Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys
                100                 105

<210> SEQ ID NO 8
<211> LENGTH: 123
<212> TYPE: PRT
<213> ORGANISM: Artificial Sequence
<220> FEATURE:
<223> OTHER INFORMATION: Heavy variable region

<400> SEQUENCE: 8

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Met
            35                  40                  45

Gly Glu Ile Asn Pro Asn Ser Gly Gly Ala Gly Tyr Asn Gln Lys Phe
     50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
                100                 105                 110

Trp Gly Gln Gly Thr Thr Val Thr Val Ser Ser
            115                 120

<210> SEQ ID NO 9
<211> LENGTH: 214
<212> TYPE: PRT
<213> ORGANISM: Artificial Sequence
<220> FEATURE:
<223> OTHER INFORMATION: Light chain

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Leu Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 449
<212> TYPE: PRT
<213> ORGANISM: Artificial Sequence
<220> FEATURE:
<223> OTHER INFORMATION: Heavy chain

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Pro
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
            325                 330                 335

Thr Ile Ser Lys Thr Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 11
<211> LENGTH: 214
<212> TYPE: PRT
<213> ORGANISM: Artificial Sequence
<220> FEATURE:
<223> OTHER INFORMATION: Light chain

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
            85                  90                  95

Thr Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 12
<211> LENGTH: 449
<212> TYPE: PRT
<213> ORGANISM: Artificial Sequence
<220> FEATURE:
<223> OTHER INFORMATION: Heavy chain

<400> SEQUENCE: 12

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Asn Met His Trp Val Arg Gln Ala Pro Gly Gln Gly Leu Glu Trp Met
        35                  40                  45
Gly Glu Ile Asn Pro Asn Ser Gly Gly Ala Gly Tyr Asn Gln Lys Phe
    50                  55                  60
Lys Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Leu Gly Tyr Asp Asp Ile Tyr Asp Asp Trp Tyr Phe Asp Val
            100                 105                 110
Trp Gly Gln Gly Thr Thr Val Thr Val Ser Ser Ala Ser Thr Lys Gly
        115                 120                 125
Pro Ser Val Phe Pro Leu Ala Pro Cys Ser Arg Ser Thr Ser Glu Ser
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Asn Phe Gly Thr Gln Thr Tyr Thr Cys Asn Val
        195                 200                 205
Asp His Lys Pro Ser Asn Thr Lys Val Asp Lys Thr Val Glu Arg Lys
    210                 215                 220
Cys Cys Val Glu Cys Pro Pro Cys Pro Ala Pro Pro Val Ala Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Phe Arg Val
    290                 295                 300
```

```
Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys
```